United States Patent
Romo et al.

(10) Patent No.: US 11,072,647 B2
(45) Date of Patent: Jul. 27, 2021

(54) TGF-RECEPTOR II ISOFORM, FUSION PEPTIDE, METHODS OF TREATMENT AND METHODS IN VITRO

(71) Applicants: Ana Romo, Buenos Aires (AR); Anabela Belen La Colla, Buenos Aires (AR); Matias Adan Preisegger, Buenos Aires (AR); Marcela Soledad Bertolio, Buenos Aires (AR); Ricardo Alfredo Dewey, Buenos Aires (AR); Pamela Daiana Vazquez, Buenos Aires (AR); Andrea Nancy Chisari, Buenos Aires (AR); Tania Melina Rodriguez, Buenos Aires (AR); Benito Jorge Velasco Zamora, Buenos Aires (AR)

(72) Inventors: Ana Romo, Buenos Aires (AR); Anabela Belen La Colla, Buenos Aires (AR); Matias Adan Preisegger, Buenos Aires (AR); Marcela Soledad Bertolio, Buenos Aires (AR); Ricardo Alfredo Dewey, Buenos Aires (AR); Pamela Daiana Vazquez, Buenos Aires (AR); Andrea Nancy Chisari, Buenos Aires (AR); Tania Melina Rodriguez, Buenos Aires (AR); Benito Jorge Velasco Zamora, Buenos Aires (AR)

(73) Assignees: Onsejo Nacional DE Investigation Cientiticay Tecnica, Buenos Aires (AR); Fundocion Articula, Buenos Aires (AR); INIS Biotech LLC

(*) Notice: Subject to any disclaimer, the term of this patent is extended or adjusted under 35 U.S.C. 154(b) by 47 days.

(21) Appl. No.: 16/173,426

(22) Filed: Oct. 29, 2018

(65) Prior Publication Data
US 2019/0112352 A1 Apr. 18, 2019

Related U.S. Application Data

(63) Continuation-in-part of application No. 15/105,162, filed as application No. PCT/US2014/071338 on Dec. 19, 2014, now Pat. No. 10,233,227.

(60) Provisional application No. 61/917,974, filed on Dec. 19, 2013.

(51) Int. Cl.
| | |
|---|---|
| C07K 14/71 | (2006.01) |
| C12N 15/62 | (2006.01) |
| C12N 15/63 | (2006.01) |
| C07K 16/28 | (2006.01) |
| C12N 7/00 | (2006.01) |
| A61P 1/16 | (2006.01) |
| A61P 35/00 | (2006.01) |
| G01N 33/68 | (2006.01) |
| A61K 9/00 | (2006.01) |
| A61K 9/51 | (2006.01) |
| A61K 38/00 | (2006.01) |

(52) U.S. Cl.
CPC ............ *C07K 14/71* (2013.01); *A61K 9/0019* (2013.01); *A61K 9/5184* (2013.01); *A61P 1/16* (2018.01); *A61P 35/00* (2018.01); *C07K 16/2863* (2013.01); *C12N 7/00* (2013.01); *G01N 33/6872* (2013.01); *G01N 33/6893* (2013.01); *A61K 38/00* (2013.01); *C07K 2317/34* (2013.01); *C07K 2319/30* (2013.01); *C12N 2740/15043* (2013.01); *C12N 2740/16043* (2013.01); *G01N 2333/71* (2013.01); *G01N 2800/102* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 5,288,931 | A * | 2/1994 | Chang ............... | C07K 1/1133 435/69.1 |
| 7,112,660 | B1 * | 9/2006 | Domingues ........ | C07K 14/5406 530/351 |
| 2003/0045474 | A1 * | 3/2003 | Sailer ................... | A61P 19/00 514/8.8 |
| 2014/0154743 | A1 * | 6/2014 | Levy .................... | C07K 16/00 435/69.6 |

OTHER PUBLICATIONS

Tokuriki et al., 2009, Curr. Opin. Struc. Biol. 19:596-604.*
Bhattacharya et al. (2017, PLoS ONE 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Yang et al. (2002, J. Clin. Invest. 109(12):1607-1615).*

* cited by examiner

*Primary Examiner* — Elizabeth C. Kemmerer
(74) *Attorney, Agent, or Firm* — Defillo & Associates, Inc.; Evelyn A. Defillo

(57) ABSTRACT

An isoform of the TGF beta receptor II comprising a sequence of about of 80 amino acids and lacking a transmembrane domain. The isoform comprises the amino acid sequence set forth in SEQ ID No. 12. The isoform may have the amino acid sequence set forth in SEQ ID No. 2 or sequences having at least 85% sequence identity to the sequence set forth in SEQ ID No. 2. A fusion peptide is provided comprising an isoform of the TGF beta II receptor fused to a ligand, wherein a vector comprising the fusion peptide is used to treat cancer and/or hepatic fibrosis. An antibody binding the soluble isoform of the TGF beta II receptor is provided. The antibody binds the amino acid sequence shown in SEQ ID No. 12 and is used in in vitro methods.

5 Claims, 26 Drawing Sheets

Specification includes a Sequence Listing.

```
                                AgeI/------------------Exon I-----------------
(Seq ID No 13) TβRII-B   ACCGGTATGGGTCGGGGGCTGCTCAGGGGCCTGTGGCCGCTGCACATCGTCCTGTGGACG
(Seq ID No 14) TβRII-A   ACCGGTATGGGTCGGGGGCTGCTCAGGGGCCTGTGGCCGCTGCACATCGTCCTGTGGACG
(Seq ID No 1)  TβRII-SE  ACCGGTATGGGTCGGGGGCTGCTCAGGGGCCTGTGGCCGCTGCACATCGTCCTGTGGACG
                         ************************************************************

------------------Exon I----------------------/
(Seq ID No 13) TβRII-B   CGTATCGCCAGCACGATCCCACCGCACGTTCAGAAGTCGGATGTGGAAATGGAGGCCCAG
(Seq ID No 14) TβRII-A   CGTATCGCCAGCACGATCCCACCGCACGTTCAGAAGTCGGTT------------------
(Seq ID No 1)  TβRII-SE  CGTATCGCCAGCACGATCCCACCGCACGTTCAGAAGTCGGTT------------------
                         ****************************************:*

/---
(Seq ID No 13) TβRII-B   AAAGATGAAATCATCTGCCCCAGCTGTAATAGGACTGCCCATCCACTGAGACATATTAAT
(Seq ID No 14) TβRII-A   ---------------------------------------------------------AAT
(Seq ID No 1)  TβRII-SE  ---------------------------------------------------------AAT
                                                                                  ***

--------------------------Exon II---------------------------
(Seq ID No 13) TβRII-B   AACGACATGATAGTCACTGACAACAACGGTGCAGTCAAGTTTCCACAACTGTGTAAATTT
(Seq ID No 14) TβRII-A   AACGACATGATAGTCACTGACAACAACGGTGCAGTCAAGTTTCCACAACTGTGTAAATTT
(Seq ID No 1)  TβRII-SE  AACGACATGATAGTCACTGACAACAACGGTGCAGTCAAGTTTCCACAACTGTGTAAATTT
                         ************************************************************

---------------------Exon II--------------------------------
(Seq ID No 13) TβRII-B   TGTGATGTGAGATTTTCCACCTGTGACAACCAGAAATCCTGCATGAGCAACTGCAGCATC
(Seq ID No 14) TβRII-A   TGTGATGTGAGATTTTCCACCTGTGACAACCAGAAATCCTGCATGAGCAACTGCAGCATC
(Seq ID No 1)  TβRII-SE  TGTGATGTGAGATTTTCCACCTGTGACAACCAGAAATCCTG▒▒▒▒▒▒▒▒▒▒▒▒▒▒▒▒▒▒▒
                         *****************************************

----------------Exon II-----------------/-----Exon III--
(Seq ID No 13) TβRII-B   ACCTCCATCTGTGAGAAGCCACAGGAAGTCTGTGTGGCTGTATGGAGAAAGAATGACGAG
(Seq ID No 14) TβRII-A   ACCTCCATCTGTGAGAAGCCACAGGAAGTCTGTGTGGCTGTATGGAGAAAGAATGACGAG
(Seq ID No 1)  TβRII-SE  ▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒

----------------------Exon III-------------------------
(Seq ID No 13) TβRII-B   AACATAACACTAGAGACAGTTTGCCATGACCCCAAGCTCCCCTACCATGACTTTATTCTG
(Seq ID No 14) TβRII-A   AACATAACACTAGAGACAGTTTGCCATGACCCCAAGCTCCCCTACCATGACTTTATTCTG
(Seq ID No 1)  TβRII-SE  ▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒

------------------------Exon III----------------------------
(Seq ID No 13) TβRII-B   GAAGATGCTGCTTCTCCAAAGTGCATTATGAAGGAAAAAAAAAGCCTGGTGAGACTTTC
(Seq ID No 14) TβRII-A   GAAGATGCTGCTTCTCCAAAGTGCATTATGAAGGAAAAAAAAAGCCTGGTGAGACTTTC
(Seq ID No 1)  TβRII-SE  ▒▒▒▒▒▒▒▒▒▒▒▒▒▒CTTCTCCAAAGTGCATTATGAAGGAAAAAAAAAGCCTGGTGAGACTTTC
                                       *********************************************

---------------------Exon III----------------------/-----
(Seq ID No 13) TβRII-B   TTCATGTGTTCCTGTAGCTCTGATGAGTGCAATGACAACATCATCTTCTCAGAAGAATAT
(Seq ID No 14) TβRII-A   TTCATGTGTTCCTGTAGCTCTGATGAGTGCAATGACAACATCATCTTCTCAGAAGAATAT
(Seq ID No 1)  TβRII-SE  TTCATGTGTTCCTGTAGCTCTGATGAGTGCAATGACAACATCATCTTCTCAGAAGAATAT
                         ************************************************************

-------------------------Exon IV---------------------------
(Seq ID No 13) TβRII-B   AACACCAGCAATCCTGACTTGTTGCTAGTCATATTTCAAGTGACAGGCATCAGCCTCCTG
(Seq ID No 14) TβRII-A   AACACCAGCAATCCTGACTTGTTGCTAGTCATATTTCAAGTGACAGGCATCAGCCTCCTG
(Seq ID No 1)  TβRII-SE  AACACCAGCAATCCTGACTTGTTGCTAGTCATATTTCAAGTGACAGGCATCAGCCTCCTG
                         ************************************************************

---------------------Exon IV----------------------- SalI
(Seq ID No 13) TβRII-B   CCACCACTGGGAGTTGCCATATCTGTCATCATCATCTTCTACTGCTACTGAGTCGAG
(Seq ID No 14) TβRII-A   CCACCACTGGGAGTTGCCATATCTGTCATCATCATCTTCTACTGCTACTGAGTCGAG
(Seq ID No 1)  TβRII-SE  CCACCACTGGGAGTTGCCATATCTGTCATCATCATCTTCTACTGCTACTGAGTCGAG
                         *********************************************************
```

Figure 3

Signal Peptide

| | | | |
|---|---|---|---|
| (Seq ID Nº 2) TβRII-SE | MGRGLLRGLWPLHIVLWTRIAST | PPHVQKS---------------------- | -----VNND 35 |
| (Seq ID Nº 16) TβRII-A | MGRGLLRGLWPLHIVLWTRIAST | PPHVQKS---------------------- | -----VNND 35 |
| (Seq ID Nº 15) TβRII-B | MGRGLLRGLWPLHIVLWTRIAST | PPHVQKSDVEMEAQKDEIICPSCNRTAHPLRHINND 60 |

| | | |
|---|---|---|
| (Seq ID Nº 2) TβRII-SE | MIVTDNNGAVKFPQLCKFCDVRFSTCDNQKSFSKVHYEGKKKAW------------------- | 80 |
| (Seq ID Nº 16) TβRII-A | MIVTDNNGAVKFPQLCKFCDVRFSTCDNQKSCMSNCSITSCEKPQEVCVAVWRKNDENI | 95 |
| (Seq ID Nº 15) TβRII-B | MIVTDNNGAVKFPQLCKFCDVRFSTCDNQKSCMSNCSITSCEKPQEVCVAVWRKNDENI | 120 |

| | | |
|---|---|---|
| (Seq ID No 2) TβRII-SE | ------------------------------------------------------------ | 80 |
| (Seq ID No 16) TβRII-A | TLETVCHDPKLPYHDFILEDAASPKCIMKEKKKPGETFFMCSCSSDECNDNIIFSEEYNT | 155 |
| (Seq ID No 15) TβRII-B | TLETVCHDPKLPYHDFILEDAASPKCIMKEKKKPGETFFMCSCSSDECNDNIIFSEEYNT | 180 |

Transmembrane Domain

| | | |
|---|---|---|
| (Seq ID No 2) TβRII-SE | ------------------------------------ | 80 |
| (Seq ID No 16) TβRII-A | SNPDLLLVIFQ VTGISLLPPLGVAISVIIFYCY | 189 |
| (Seq ID No 15) TβRII-B | SNPDLLLVIFQ VTGISLLPPLGVAISVIIFYCY | 214 |

Figure 4

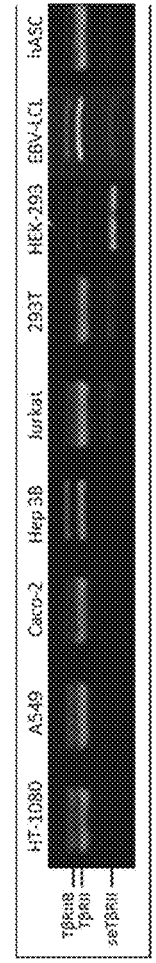

Figure 5

```
(Seq ID No 2) TßRII-SE        MGRGLLRGLW PLHIVLWTRI ASTIPPHVQK SVNNDMIVTD NNGAVKFPQL CKFCDVRFST CDNQKSCFSK
(Seq ID No 6) coTßRII-SE/FC  MGRGLLRGLW PLHIVLWTRI ASTIPPHVQK SVNNDMIVTD NNGAVKFPQL CKFCDVRFST CDNQKSCFSK (Seq ID No 2) TßRII-SE        VHYEGKKKAW *
(Seq ID No 6) coTßRII-SE/FC  VHYEGKKKAW RSDKTHTCPP CPAPELLGGP SVFLFPPKPK DQLMISRTPE VTCVVVDVSH EDPEVKFNWY (Seq ID No 2) TßRII-SE
(Seq ID No 6) coTßRII-SE/FC  VDGVEVHNAK TKPREEQYNS TYRVVSVLTV LHQDWLNGKE YKCKVSNKAL PAPIEKTISK AKGQPREPQV (Seq ID No 2) TßRII-SE
(Seq ID No 6) coTßRII-SE/FC  YTLPPSREEM TKNQVSLTCL VKGFYPSDIA VEWESNGQPE NNYKTTPPVL DSDGSFFLYS KLTVDKSRWQ (Seq ID No 2) TßRII-SE
(Seq ID No 6) coTßRII-SE/FC  QGNVFSCSVL HEALHNHYTQ KSLSLSPGK*
```

A
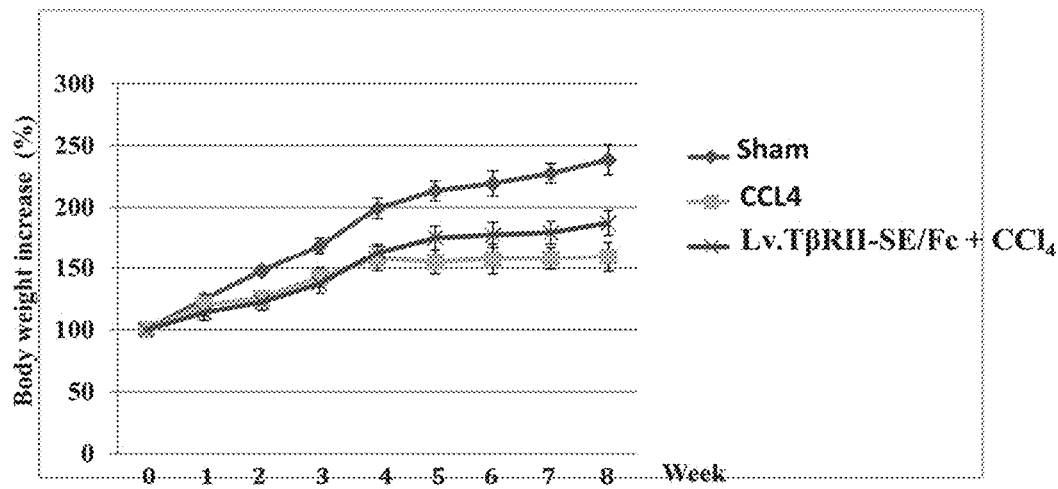
B
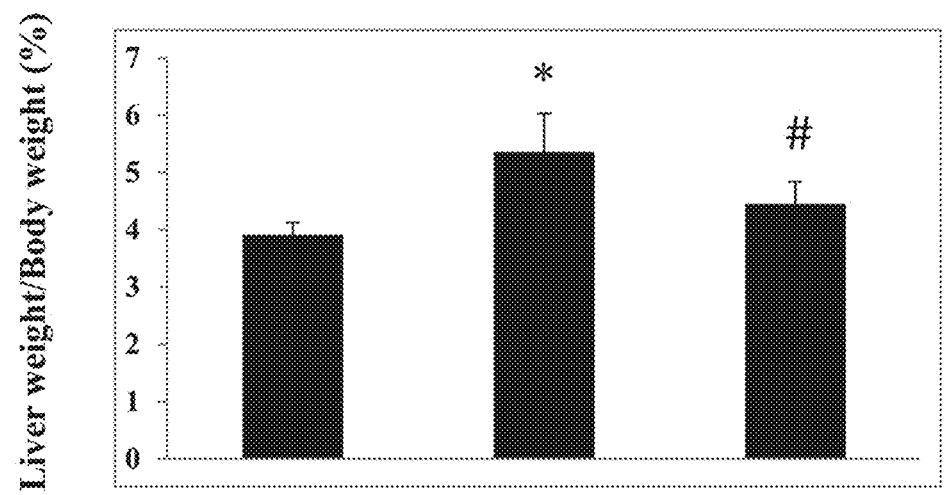
| Sham | + | + | + |
| CCl$_4$ | - | + | + |
| Lv.TβRII-SE/Fc | - | - | + |
Figure 25 ns to an isoform of the TGF-β receptor II, codifying polynucleotides, vectors, cells, transformed peptides, and fusion peptides, method and uses.
TGF-RECEPTOR II ISOFORM, FUSION PEPTIDE, METHODS OF TREATMENT AND METHODS IN VITRO

CROSS REFERENCE TO RELATED APPLICATION

This application is a continuation-in-part of U.S. application Ser. No. 15/105,162 filed Jun. 16, 2016, entitled, ISOFORM OF THE TGF-BETA RECEPTOR II, now U.S. Pat. No. 10,233,227 issued on Mar. 19, 2019, which is a national stage entry of PCT/US2014/071338 filed Dec. 19, 2014, under the International Convention claiming priority over U.S. Provisional Patent Application No. 61/917,974 filed Dec. 19, 2013, the content of which are incorporated herein by reference.

FIELD OF THE INVENTION

The present invention refers to an isoform of the TGF-β receptor II, codifying polynucleotides, vectors, cells, transformed peptides, and fusion peptides, method and uses. More specifically, it refers to an isoform of the TGF-beta receptor II comprising a sequence of about 80 amino acids and lacking a transmembrane domain. The isoform comprises the amino acid sequence of SEQ ID No. 12. The isoform may have the amino acid sequence set forth in SEQ ID No. 2 or sequences having at least 85% sequence identity to the sequence set forth in SEQ ID No. 2.

BACKGROUND OF THE INVENTION

Transforming growth factor-beta (TGF-β) is abundant in bone matrix and has been shown to regulate the activity of osteoblasts and osteoclasts in vitro and in vivo. Human Adipose derived Mesenchymal Stromal Cells (ASC) are precursors of osteoblasts, adipoblasts and chondroblasts. Thus, studies initially focused on the secretion of cytokines by ASC which have a profound effect in bone remodeling, such as Tgf-β1, Osteoprotegerin (OPG) and Hepatocyte Growth Factor (HGF).

TGF-β1 concentrations are high in subchondral bone from humans with osteoarthritis. High concentrations of TGF-β1 induced formation of nestin-positive mesenchymal stem cell (MSC) clusters, leading to formation of marrow osteoid islets accompanied by high levels of angiogenesis (Zhen G, et al. (*Nat Med.* 19: 704-12, 2013). It has been found that transgenic expression of active TGF-β1 in osteoblastic cells induced osteoarthritis, whereas inhibition of TGF-β activity, by means of a TβRII dominant negative receptor, in subchondral bone, attenuated the degeneration of articular cartilage leading to less development of osteoarthritis. It has also been reported that mice expressing a dominant negative type II TGF-β receptor (TβRII-DN) in osteoblasts, show decreased TGF-β responsiveness in osteoblasts and increased bone volume, demonstrating that endogenous TGF-beta acts directly on osteoblasts to regulate bone remodeling, structure and biomechanical properties (Filvaroff, E. et al. *Development,* 126: 4267-4279, 1999). In addition, TGF-β also regulates osteoclastogenesis and osteoclast survival, in part through the induction of osteoprotegerin (OPG), a protein known to inhibit osteoclast formation and function (Thirunavukkarasu K, et al. *J. Biol. Chem.* 276:36241-36250, 2001).

Transgenic mice that overexpress the dominant-negative type II TGF-β receptor (dnTgfbr2) in skeletal tissue exhibit progressive skeletal degeneration (Buckwalter J A, et al. *Clin Orthop Relat Res* 423: 7-16, 2004). The articular chondrocytes in the superficial zone of cartilage tissue become hypertrophic with increased type X collagen expression. Loss of proteoglycan and progressive degradation of cartilage tissue have been observed in 6-month-old mice which strongly resemble human osteoarthritis (OA) (OA-like) (Serra R, et al. *J Cell Biol* 139: 541-552, 1997). TGF-β signaling plays a critical role not only in the regulation of chondrocyte homeostasis during cartilage destruction, but also in the manipulation of subchondral bone cell behavior during osteophyte formation, another feature of OA (van der Kraan P M, et al. *Osteoarthr Cartilage* 15: 237-244, 2007).

The role of the TGF-β signaling pathway in osteophyte formation was further explored by blocking studies using specific TGF-β inhibitors. Several groups demonstrated that ablation of endogenous TGF-β activity, by intra-articular overexpression of soluble TGF-β type II receptor extracellular domain or Smad7, suppresses osteophyte formation in experimental murine OA models (Scharstuhl A, et al. *J Immunol* 169: 507-514, 2002). These observations clearly demonstrate that TGF-β plays a dominant role in the induction of osteophytes, at least in murine OA models.

In vivo, TGF-β1 also induces angiogenesis (Madri J A, et al. *J Cell Biol.* 106: 1375-1384, 1988; Roberts Aft *Proc Natl Acad Sci USA.* 83: 4167-4171, 1986; Yang E Y, et al. *J Cell Biol.* 111: 731-741, 1990). In OA, high TGF-β1 levels are also accompanied by high levels of angiogenesis. Hepatocyte growth factor (HGF) is a potent mitogen, morphogen, and motogen for a variety of cells, mainly epithelial cells. Increased expression of the HGF/HGF-receptor system in osteoarthritic cartilage, suggest a regulatory role in the homeostasis and pathogenesis of human joint cartilage (Pfander D, et al. *Osteoarthritis Cartilage.* 7: 548-59, 1999).

Previous studies have shown that TGF-β can promote angiogenesis and tumor invasion via stimulation of HGF expression (Chu S H, et al. *J Neurooncol.*, 85: 33-38, 2007; Lewis M P, et al. *Br J Cancer* 90: 822-832, 2004)). Conversely, TGF-β has also been shown to inhibit HGF transcription, potentially through binding of a TGF-β inhibitory element located approximately 400 bp upstream of the HGF transcription start site (Liu Y, et. al. *J Biol Chem.*, 269: 4152-4160, 1994; Plaschke-Schlütter A, et al. *J Biol Chem.*, 270: 830-836, 1995), and abrogation of this effect leads to cancer development (Cheng N, et al. *Cancer Res.* 67: 4869-4877, 2007).

Quinolones (QNs) antibiotics such as Ciprofloxacin (CPFX) were widely used in clinical practice owing to their wide spectrum antibacterial activity and high degree of bioavailability. They were not approved for use in children and adolescents due their toxic effects on joint cartilage of immature animals (Cuzzolin L, et al. *Expert Opin Drug Saf* 1: 319-24, 2002). Quinolones, administered systemically, caused arthropathy and tendinopathy when given during the growth phase (Sendzik J, et al. *Int J Antimicrob Agents* 33: 194-200, 2009). It was reported that Ciprofloxacin decreased thickness of articular cartilage of the femoral condyle, inhibit proliferation of cultivated chondrocytes and secretion of soluble proteoglycans in a concentration- and time-dependent manner in juvenile rats (Li, P. et al. *Arch. Pharmacol. Sin.* 25: 1262-1266, 2004).

Chondrocyte cluster formation is a feature of all mechanical and chemical OA models (Moriizumi T, et al. *Virchows Arch B Cell Pathol Incl Mol Pathol.*, 51: 461-474, 1986; van der Kraan P M, et al. *Am J Pathol.*, 135:1001-1014, 1989). Animals with quinolone arthropathy showed cavities in the middle zone of the articular cartilage containing necrotic chondrocytes. After 14 days, many of the lacunae in defective areas contained chondrocyte clusters. When treated for 14 days, and after a 14-day recovery period, territorial matrix had been deposited around individual chondrocytes within the clusters, indicating that in immature joints there is a certain degree of spontaneous repair by cluster cells (Sharpnack D D, et al. *Lab Anim Sci.*, 44: 436-442, 1994). It has been shown that TGF-β1 is activated in the subchondral bone in response to altered mechanical loading in an anterior cruciate ligament transection (ACLT) osteoarthritis mouse model (Zhen G, et al. *Nat Med.* 19: 704-12, 2013). Additionally, CPFX was found to up-regulate TGF-β1 production by HT-29 cells and its anti-proliferative effect was abolished when TGF-β1 was blocked (Bourikas L A, et al. *Br J Pharmacol.* 157: 362-70, 2009).

Adipose derived stem cells (hASCs) express cytokines such as IL-6, GM-CSF and Flt3-ligand (Tholpady S S, et al. *Clin Plast Surg* 33: 55-62, 2006; Katz A J, et al. *Stem Cells.* 23: 412-23, 2005; Schäfer A, et al. *Stem Cells* 25: 818-827, 2007). These cytokines are regulated by TGF-β1 either negatively (GM-CSF, SCF and Flt3-ligand) (Jacobsen S E, et al. *J Immunol.*, 151: 4534-4544, 1993; Jacobsen S E, et al. *Blood* 87: 5016-5026, 1996) or positively (IL-6, TPO) (Ramsfjell V, et al. *J Immunol.* 158: 5169-5177, 1997). Recently, overexpression of a dominant negative mutant of the human TβRII receptor (TβRII-DN) in mammalian cells has been shown to be very effective in blocking TGF-β1 action. This mutant, based on the isoform A of the receptor, is capable to bind TGF-β1 but signaling is disrupted due to the absence of a serine/threonine kinase domain. TβRIIA-DN has been shown to disrupt TGF-β1 mediated signaling allowing the study of the behavior of different cell types in the absence of either a paracrine or an autocrine effect of the cytokine (Fan X, et al. *The Journal of Immunology* 168: 755-762, 2002).

Various documents disclosing different TGF-β1 receptors, chimerics, fusion proteins, domains, are known, for example, EP0975771, WO 2008/157367, US 2006/0247198, U.S. Pat. No. 6,001,969, and WO 94/09815.

SUMMARY OF THE INVENTION

A soluble isolated isoform of the TGF beta II receptor is provided comprising a sequence of about 80 amino acids and lacking the transmembrane domain; wherein the isoform would be acting as a TGFβ-1 agonist. In a preferred embodiment, the amino acid sequence of the isoform has at least 85%, 90%, 95%, or 99% identity with the amino acid sequence set forth in SEQ ID No. 2. The isoform comprises within its sequence the peptide disclosed in SEQ ID No. 12.

A polynucleotide encoding a soluble isoform of the TGF beta II receptor is provided, which in a preferred embodiment has at least 90%, 95%, or 99% identity with the nucleotide sequence of SEQ ID No. 1. In another preferred embodiment, the polynucleotide further comprises a Kozak sequence.

A fusion peptide is provided comprising an isoform of the TGF beta II receptor fused to a ligand. In a preferred embodiment the isoform is an amino acid sequence having at least 85% sequence identity to SEQ ID No. 2 and the ligand is the Fc of an immunoglobulin.

An antibody binding the soluble isoform of the TGF beta II receptor is provided. In a preferred embodiment, the antibody binds the amino acid sequence shown in SEQ ID No. 12.

A method of treating diseases associated to TGF-β dysregulation is provided, comprising administering to a mammal in need thereof the soluble isoform of the TGF beta receptor.

A method of treating diseases associated to TGF-β dysregulation is provided, comprising administering to a mammal in need thereof an antibody binding the soluble isoform of the TGF beta II receptor. In a preferred embodiment the antibody recognizes and binds the amino acid sequence shown in SEQ ID No. 12. The associated diseases may be selected from any disorder related to dysregulation of TGF-β signals, such as cancer, fibrosis, and cardiovascular diseases; metabolic and musculoskeletal defects, mutations in TβRII (TGFBR2 gene), for example, Loeys-Dietz syndrome (LDS), Marfan syndrome type 2 (MFS2), or different aneurisms (FTAAD).

DESCRIPTION OF THE DRAWINGS

FIG. 3 shows the alignment of partial cDNA sequences of the two known TβRII (A and B) isoforms, and the one disclosed in the present application (TβRII-SE); cDNA sequences include the start codon (ATG) and the last nucleotide encoding the transmembrane domain (TMD); the dark grey bar indicates an additional deletion found in exons II and III of TβRII-SE.

FIG. 4 shows alignments of partial predicted protein sequences belonging to the human TβRII isoforms A and B, and the TβRII-SE; light grey boxes show residues involved in disulfide bridges critical for receptor-ligand bonding (C54-C71, C61-C67); dark grey boxes show residues which are fundamental for interaction with TGF-β (D55, I76, E142).

FIG. 5 shows the results of detection by RT-PCR of the different TβRII isoforms (A, B and SE) in different human cell types; HT1080 (fibrosarcoma), A549 (pulmonary adenocarcinoma), CaCo-2 (colorectal adenocarcinoma), Hep3B (hepatic carcinoma), Jurkat (acute T-cell leukemia), 293T (epithelial cells from embryonic kidney immortalized with the SV40 virus large T-antigen), HEK-293 (epithelial cells from embryonic kidney immortalized with adenovirus), EBV-LCL (lymphoblastoid cell line immortalized with the Epstein-Barr virus), and hASC (stromal mesenchymal cells from human adipose tissue).

FIG. 19 shows protein alignment to compare changes made to the recombinant TβRII-SE. coTβRII-Se was fused "in frame" to the human IgG1 Fc domain. Asterisk: Stop Codon; Black Box: linker aminoacids; Grey box: Fc domain.

FIG. 25 shows the effect of TβRII-SE/Fc overexpression on body weight and in the liver to body weight ratio in $CCl_4$-induced liver fibrosis in rats. A) Body weight gain (%) of animals in the different experimental groups. B) Liver to body weight ratio (%) in the different experimental groups. *p<0.05: Vehicle vs $CCl_4$; #p<0.05: $CCl_4$ vs Lv.TβRII-SE/Fc+$CCl_4$.

DETAILED DESCRIPTION OF THE INVENTION

A variant or isoform of the TGF beta receptor II is disclosed, which is expressed in human cells referred to herein as endogenous soluble TβRII (TβRII-SE) and that contrarily to other isoforms acts like a TGF-β1 agonist.

Figure 1:
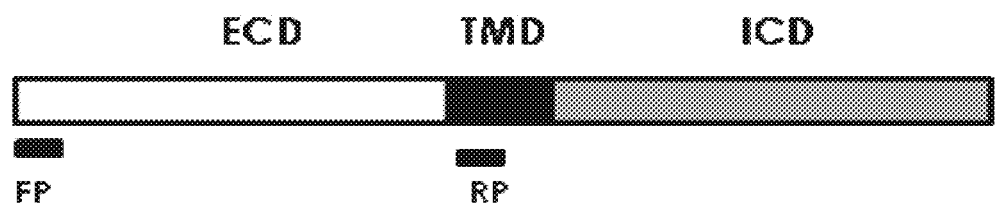
FIG. 1 shows a schematic diagram of the TβRII receptor indicating the extracellular (ECD), transmembrane (TMD) and intracellular (ICD) domains. FP and RP boxes indicate the forward and reverse primers used to amplify the TβRII cDNA by RT-PCR.

By using specific primers, a region of the human TβRII mRNA from T-lymphocytes only encoding the extracellular (ECD) and the transmembrane (TMD) domains and excluding the intracellular domain (ICD) was initially amplified by RT-PCR, (FIG. 1).

Figure 2:
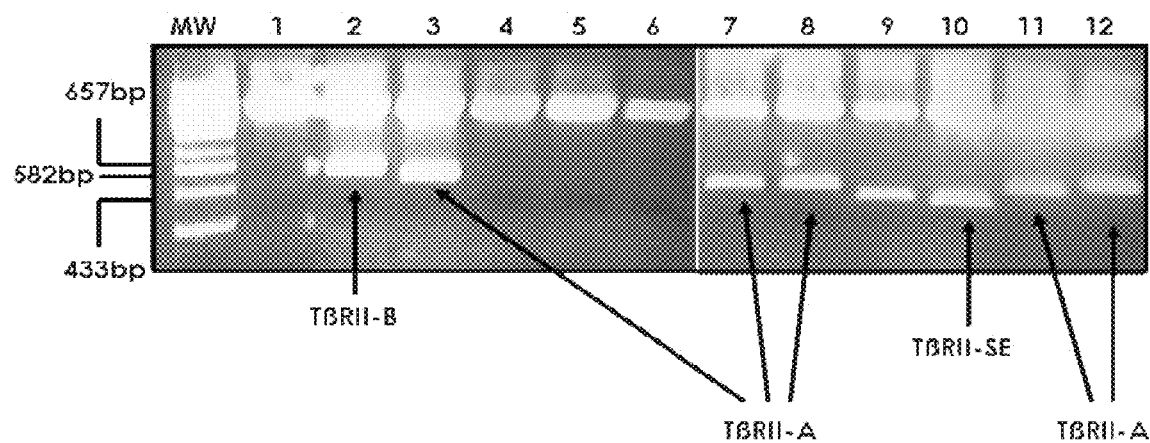
FIG. 2 shows a gel with the results of recombinant plasmid digestion containing the two already described human TβRII (A and B) isoforms and the newly described by the present inventors, TβRII-SE, obtained by RT-PCR from human lymphocytes.

After the PCR reaction, DNA products were cloned into the pGEM-T Easy plasmid. Plasmids were digested with AgeI and SalI and revealed in an agarose gel the presence of clones with inserts of three different sizes (FIG. 2). Clone 2 contained an insert of 650 bp. In clones 3, 7, 8, 11, and 12 the insert size was of 580 bp and in clone 10 the size reflected the presence of an insert of 430 bp.

DNA sequencing and BLAST alignment (NCBI) of all clones indicated that clones 3, 7, 8, 11, and 12 (582 bp) were identical to human TGF 13 receptor II variant A (TβRII-A). Additionally, clone 2 (657 bp) showed 100% identity with the isoform TβRII-B. Clone 10 (433 bp) was similar to the TβRII-A sequence but with an additional 149 bp deletion. In this clone, the last 62 bp encoded by exon II and the first 88 bp encoded by exon III were absent, TβRII-SE (SEQ ID No. 1) (FIG. 3).

The alignment of the predicted amino acid sequence of all three isoforms (FIG. 4) indicated that the deletion found in clone 10 generates a frameshift starting at amino acid 68, which adds a stop codon 13 amino acids after the deletion generating a prematurely terminated 80 amino acids long isoform lacking the transmembrane domain and this is the new isoform TβRII-SE (SEQ ID No. 2).

This isoform differs in 12 amino acids at the carboxyl end compared to the membrane bound variants of TβRII (isoforms A and B). Due to this, and according to the predicted amino acid sequence, the TβRII-SE isoform of clone 10 lacks pivotal sites for the productive action of TGF-β such as amino acid 176 of SEQ ID No. 3 that contributes to the ligand-receptor binding through hydrophobic contact; amino acid E142 of SEQ ID No. 3 which forms hydrogen bonds with R25 of TGF-β increased affinity and determined binding specificity and amino acid C71 of SEQ ID No. 3 which forms a disulfide bridge with C54 of the same receptor (see FIG. 4) necessary both for binding to the ligand and for signaling (reference, Alain Guimond, et. al. FEBS Letters 515: 13-19, 2002). Thus, the TβRII-SE isoform might not be able to bind TGF-β1 with the same affinity than that of known isoforms. Additionally, due to the premature termination, the TβRII-SE isoform lacks the amino acid sequence belonging to the transmembrane domain (TMD), showing the presence of a new endogenously secreted soluble TβRII isoform in human T-lymphocytes.

As previously mentioned, the new isoform is referred to as TβRII Soluble Endogenous (TβRII-SE). The TβRII-SE isoform is different from the secretable genetically engineered TβRII isoform. The latter is an artificial TβRII receptor with a truncated TβRII-A fused to the Fc region of human IgM and blocks the effects of TGF-6, thus acting as an antagonist (reference, R. J Akhurst. J. Clin. Invest. 109: 1533-3610, 2002).

To determine the theoretical molecular weight of the TβRII-SE isoform, post-translational modifications (PTM) predicted from the amino acid sequence (SEQ ID No. 2) were established by using different computer programs (Table 1). In this analysis, three glycation sites at K46, K52 and K78 (NetGlycate program) (Johansen, M. B.; Glycobiology 16: 844-853, 2006); three phosphorylation sites at S31, S59 and Y73 (NetPhos program) (Blom, N.; Journal of Molecular Biology 294: 1351-1362, 1999) and one site for sumoylation in K46 (SUMOplot™ program, ABGENT, CA, USA) were identified. On the other hand, sites for sulfonation, C-mannosylation, O-GalNAC glycosilation, O-glycosilation, N-glycosilation, myristoylation, and palmitoylation were not found in TβRII-SE. In this study it was estimated that the molecular weight of the mature TβRII-SE isoform was of about 18.4 kDa.

TABLE 1

In silico analysis of the TβRII-SE amino acid sequence showing predicted post-translational modifications and molecular weight with and without modifications.

| | | | |
|---|---|---|---|
| Predicted pI/ theoretical Mw | 9.64/9161.72 | | |
| pI/Mw without a signal peptide | 9.05/6532.51 | | 6,532.51 kDa |
| Secretion probability of the signal peptide | 0.960 (first 12 aa) | SignalP Program | |
| Clivage site | Between pos. 23 and 24 | SignalP Program | |
| C-mannosylation | No sites | | |
| GalNAc O-glycosylation | No sites | | |
| Glycations | 3 sites (Lys 46, 52, and 78) | NetGlycate Program | 0.558 kDa (0.186 kDa each) |
| N-glycosylations | No sites | NetNGlyc Program | |
| O-Glycosylations | No sites | (OGPT Program) | |
| O-(beta)-GlcNAc | No sites | | |
| Myristoylation | No sites | | |
| Palmitoylation | No sites | | |
| Phosphorylation | 3 sites (Ser 31 and 59, Tyr 79) | NetPhos Program | 0.285 kDa (0.095 Da each) |
| Sulfonations | No sites | | |
| Addition of SUMO protein | 1 site (Lys 46) | SUMOplot program | 11 kDa |
| Final Mw with modifications | | | 18.4 kDa |

To confirm whether TβRII-SE mRNA was also present in human cells other than lymphocytes, we amplified by RT-PCR using the same set of primers various human cell lines and primary cultures (FIG. 5). It may be observed that human solid tumor derived cell lines, for example, HT1080 (fibrosarcoma), A549 (lung adenocarcinoma), CaCo-2 (colon cancer) and Hep 3B (hepatocellular carcinoma) only showed the presence of mRNA of variants A and B, but not TβRII-SE. Additionally, in Jurkat cells (acute lymphoid leukemia), 293T cells (embryonic kidney cells immortalized with the SV40 T-antigen), HEK-293 cells (embryonic kidney cells immortalized with the adenovirus E1A protein, EBV-LCL (Lymphoblastoid Cell Line immortalized with the Epstein Barr Virus) and ASC (human adipose derived mesenchymal stem cells) passage 6 primary culture, mRNA encoding for TβRII-SE was present in all cases (FIG. 5). The presence of the TβRII-SE isoform was further confirmed by DNA sequencing.

Figure 6:
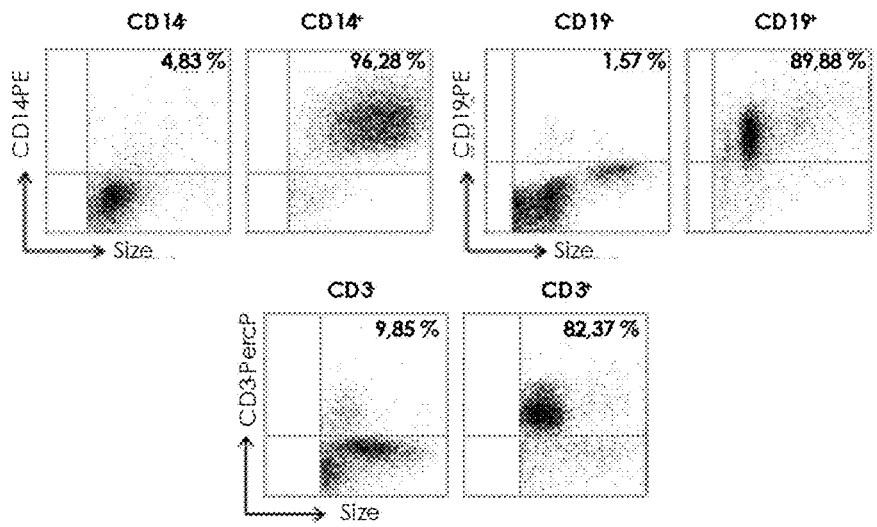
FIG. 6 shows the results obtained by flow cytometry plots showing cell purity of monocytes (CD14+), B-cells (CD19+), and T-cells (CD3+) separated by immune purification.
Figure 7:
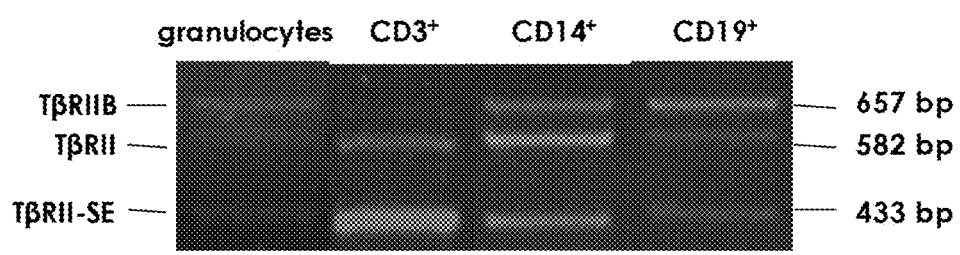
FIG. 7 shows TβRII splicing variant mRNA profiles in human leukocyte subsets, such as granulocytes, T-lymphocytes (CD3+), B lymphocytes (CD19+), and monocytes (CD14+).

To check whether TβRII-SE is also present in leukocytes different from T-lymphocytes, granulocytes, monocytes, B-cells and T-cells were purified from human peripheral blood by density gradient and subsequent magnetic immune-purification with specific monoclonal antibodies, to high purity (FIG. 6). RT-PCR analysis showed that TβRII-SE is present in all leukocyte subsets but with different expression levels (FIG. 7).

To determine whether TβRII-SE may be secreted to the extra cellular medium, TβRII-SE cDNA was cloned downstream from the ubiquitous promoter CMV in a self-inactivating (SIN) bicistronic lentiviral vector also expressing eGFP, as described in the examples, to generate the Lt-TβRII-SE vector. As a control, two lentiviral vectors were used: one bicistronic encoding a dominant negative TβRII mutant together with eGFP (Lt-TβRIIA-DN) and another encoding eGFP alone (Lt-eGFP), also under the action of the CMV promoter (FIG. 8).

Figure 8:
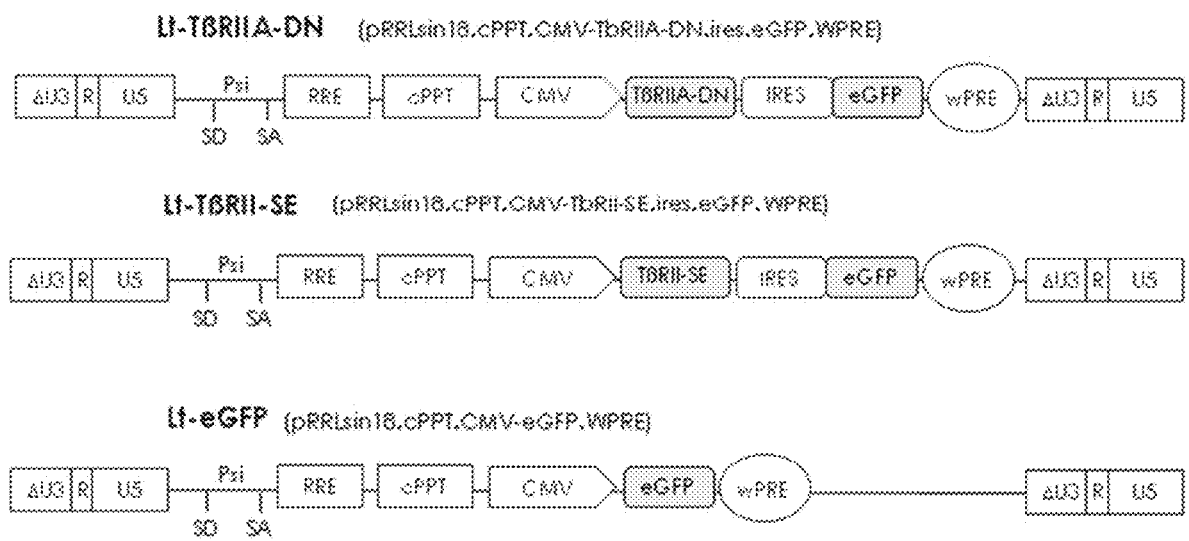
FIG. 8 shows lentiviral vectors encoding the newly described hTβRII-SE variant and a dominant negative (DN) mutant of the TβRII-A receptor under the action of the CMV promoter; as a control, a lentiviral vector encoding eGFP under the CMV promoter was used. The complete names of the vectors are indicated at the left side of the diagram. The abbreviated names are shown on top of each vector.
Figure 9:
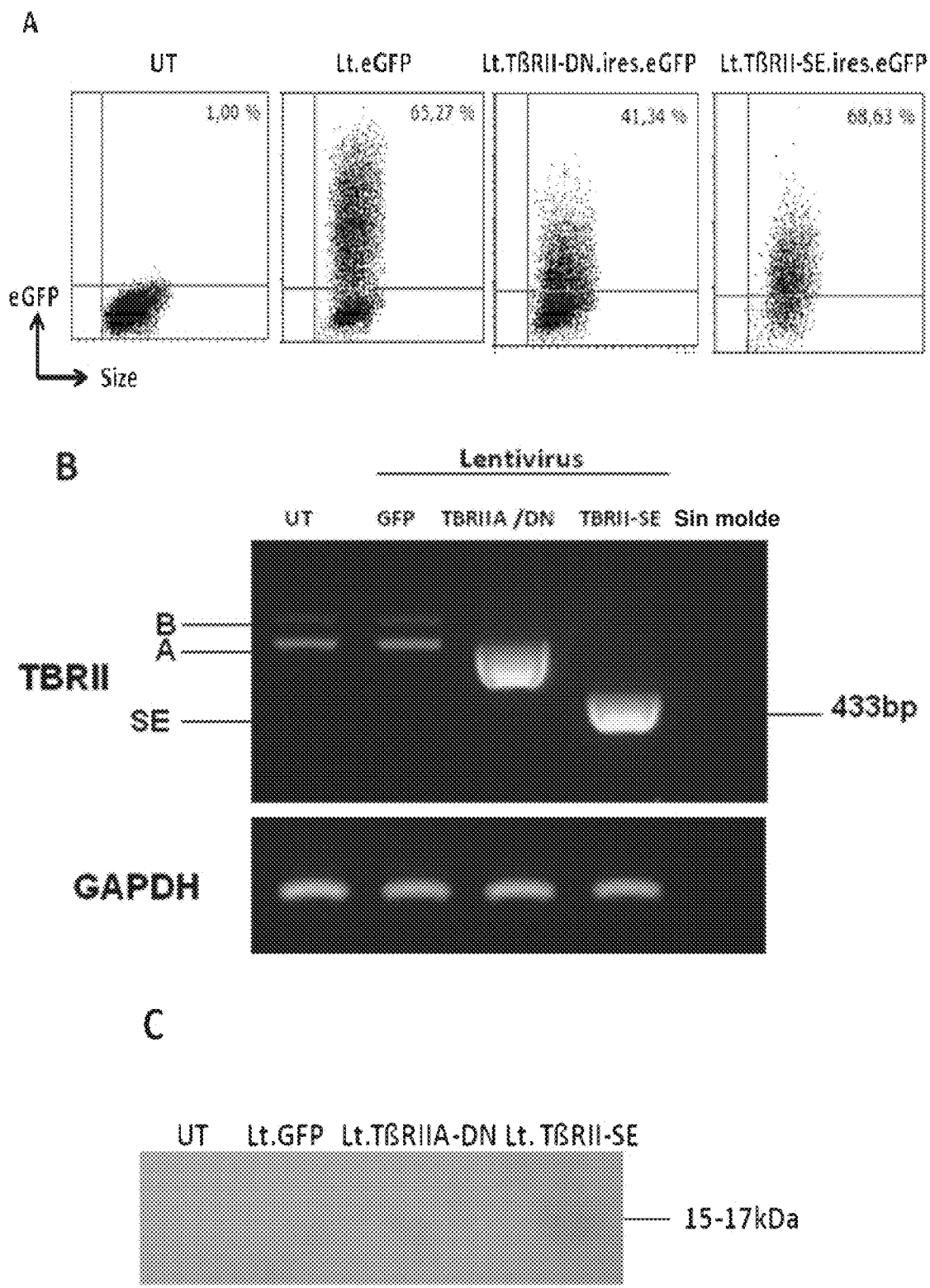
FIG. 9 shows overexpression of TβRII-SE in A549 cells. A): results of a flow cytometry analysis showing the percentage of eGFP expressing A549 cells transduced with a lentiviral vector encoding TβRII-SE (Lt-TβRII-SE) and control vectors; B): results of a RT-PCR showing overexpression of TβRII-SE at the mRNA level; C): results of a demonstration of the presence of TβRII-SE only in the supernatant of cells transduced with Lt-TβRII-SE as detected by Western blot with a TβRII specific antibody recognizing the extracellular domain.

With these lentiviral vectors, shown in FIG. 8, A549 cells were transduced, at an MOI of 50. Seventytwo hours after transduction, cell supernatants were frozen for further experiments and the percentage of eGFP expressing cells was measured by flow cytometry (FIG. 9A). In cells transduced with Lt-TβRII-SE and Lt-eGFP, 68.63% and 65.27% of the cells, respectively, showed integration of the lentiviral vector as demonstrated by eGFP expression. RT-PCR of Lt-TβRII-SE transduced cells revealed the presence of a 433 bp band, indicating overexpression at the mRNA level of the TβRII-SE isoform (FIG. 9B). Cell supernatants were thawed, and Western blotted as described in the examples (FIG. 9C). Only TβRII-SE was detected in the supernatant of Lt-TβRII-SE transduced A549 cells cultured in the presence of protease inhibitors.

The molecular weight of TβRII-SE detected by Western blot is in agreement with the predicted molecular weight, after the addition of post-translational modifications (18 kDa) (Table 1). This is the first evidence ever that there exists a new secretable TβRII receptor variant or isoform in human cells.

To show the function of the TβRII-SE isoform, functional assays were carried out wherein untransduced, expressing nearly undetectable levels of TβRII-SE, transduced with lentiviral vectors encoding eGFP alone, or bicistronics together with either TβRII-SE or the dominant negative (DN) mutant of the TβRIIA variant known to work as a TGF-β1 antagonist, A549 cells were used.

Figure 10A:
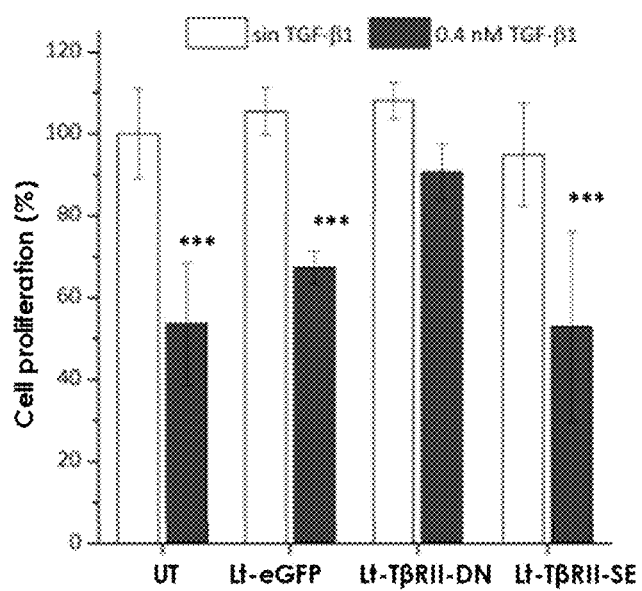
FIG. 10A shows the results of a proliferative MTT assay. A549 cells untransduced (UT) and transduced with Lt-TβRII-SE, Lt-TβRIIA-DN, and Lt-eGFP, treated with 0.4 nM TGFβ-1 and untreated.

Initially, MTT ((3-[4,5-dimethylthiazol-2-yl]-2,5-diphenyltetrazolium bromide; thiazolyl blue) assays were performed to evaluate if overexpression of TβRII-SE inhibits or not cell proliferation in the presence of 0.4 nM TGFβ-1 (FIG. 10A). As may be noted, in the presence of TGFβ-1, TβRII-SE-transduced cells proliferate significantly less than the same cells not treated with TGFβ-1 and at levels found in control untransduced cells (UT) and Lt.eGFP-transduced cells. These results indicated that TβRII-SE is not a TGFβ-1 antagonist.

Figure 10B:
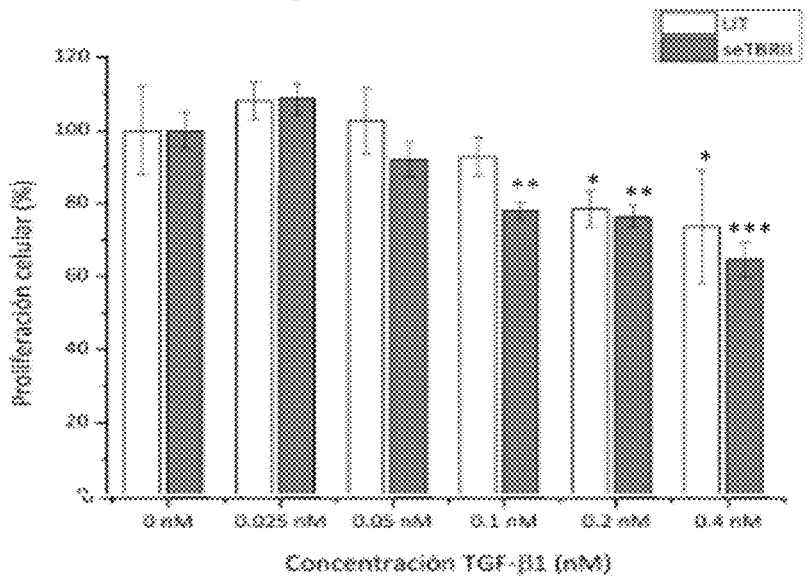
FIG. 10B shows the TGFβ-1 curve in A549 cells transduced with a lentiviral vector encoding TβRII-SE and untransduced (UT). *p<0.05; p<0.01, *p<0.001.

Additionally, to check whether TβRII-SE acts as a TGFβ-1 agonist, A459 cells either overexpressing TβRII-SE or not (untransduced cells or UT) were incubated in the presence of increasing concentrations of TGFβ-1 (FIG. 10B). These results show that in UT cells, proliferation started to decrease in the presence of 0.2 nM TGFβ-1 compared to the values obtained in the absence of TGF-β1. However, in cells overexpressing TβRII-SE, proliferation started to decrease at a TGFβ-1 concentration of 0.1 nM compared to the same cell line without the addition of TGF-β1. These results indicate that in cells overexpressing TβRII-SE, TGFβ-1 achieved the same effect than in UT cells but at half concentration, which would suggest that the TβRII-SE isoform may act as an agonist.

Figure 11A:
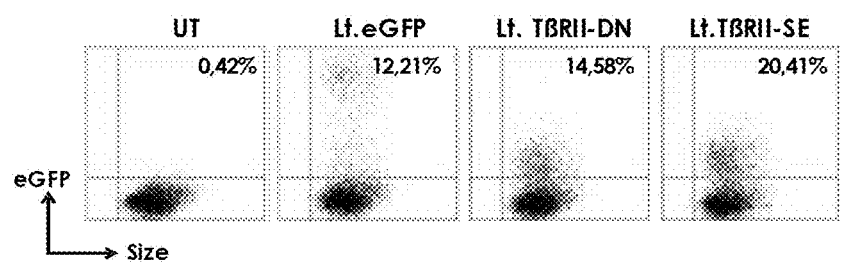
FIG. 11A shows results of a flow cytometry analysis of hASC transduced with lentiviral vectors encoding TβRII-SE, TβRIIA-DN, and eGFP; and untransduced (UT)
Figure 11B:
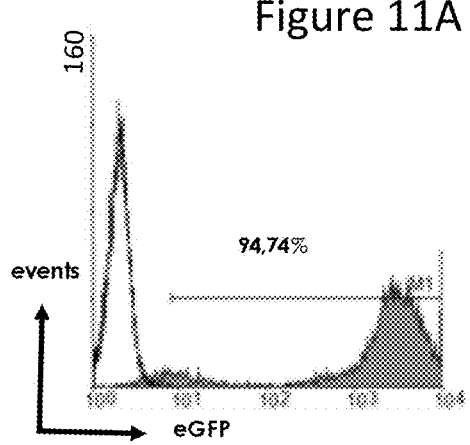
FIG. 11B shows a representative histogram showing percentage of purity after cell sorting.

To further assess the agonistic role of the TβRII-SE isoform, hASCs were transduced with Lt-TβRII-SE, Lt-TβRIIA-DN, and Lt.eGFP, at an MOI of 150 as described in the examples. Seventy two hours after transduction the percentage of eGFP expressing cells was measured by flow cytometry (FIG. 11A). For further experiments with pure cell populations, transduced cells were expanded and cell sorted in a FACSArialI Cell Sorter (Becton Dickinson, San Jose, Calif.) to a purity of eGFP-expressing cells of more than 90% (FIG. 11B), indicating that most cells overexpress the new isoform.

Figure 12:
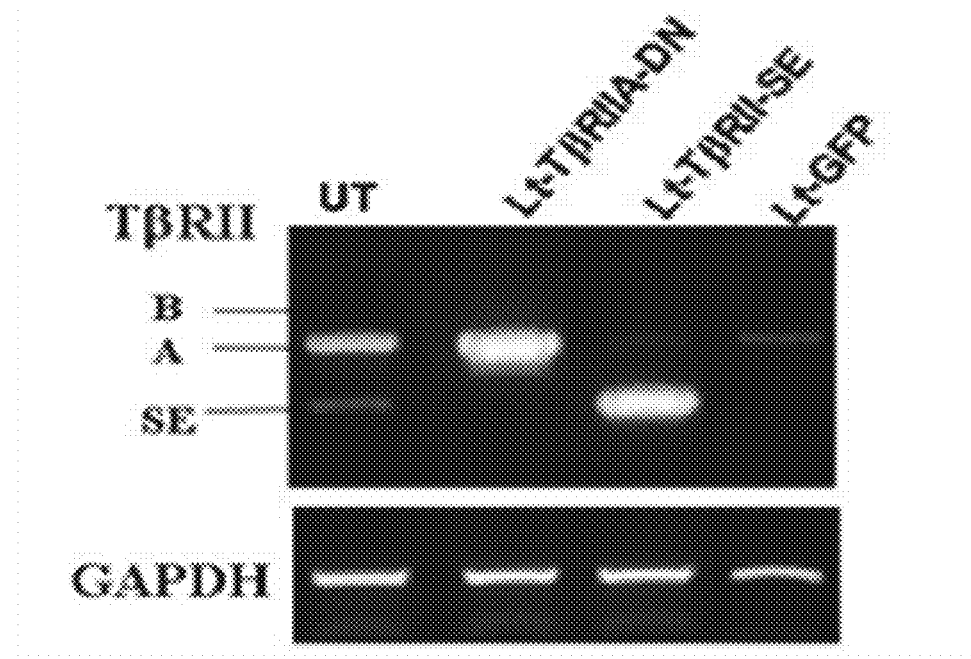
FIG. 12 shows the results of a RT-PCR analysis of hASC cells showing overexpression of TβRIIA-DN and TβRII-SE; GAPDH was used as reference gene.
Figure 13:
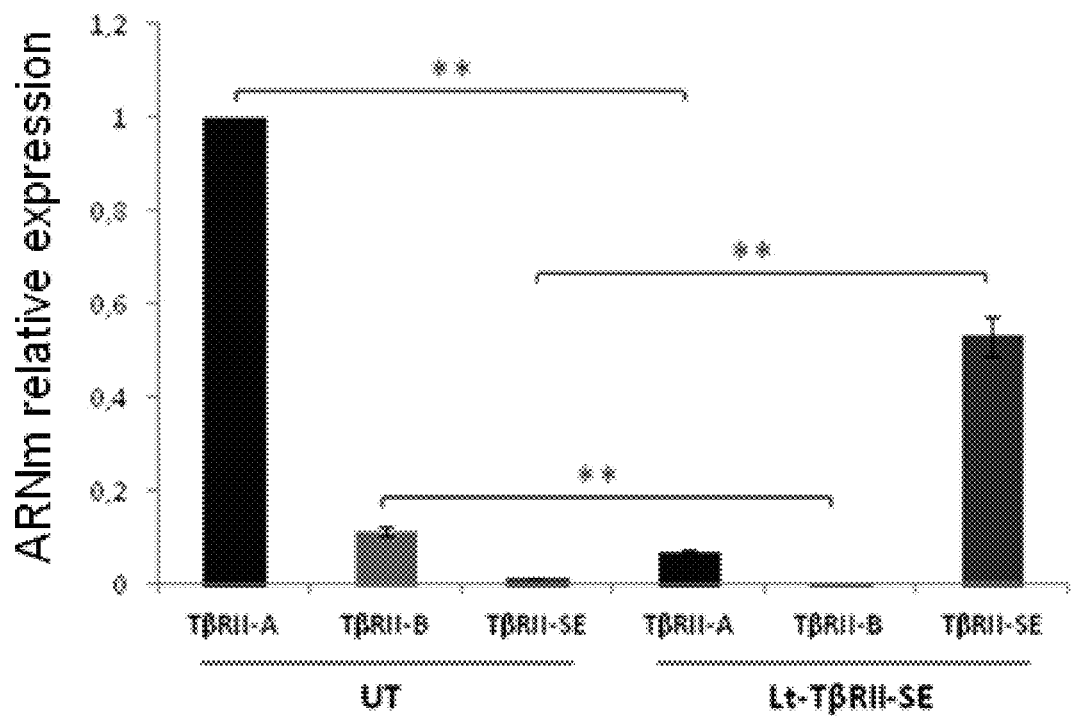
FIG. 13 shows relative mRNA levels of TβRII receptors (TβRII-A, TβRII-B and TβRII-SE) in untransduced hASCs (UT) and transduced with Lt.TβRII-SE.

RT-PCR performed on poly A+ mRNA from either transduced or untransduced hASC cells showed the pattern of TβRII isoforms expression depicted in FIG. 12. Cells overexpressing TβRII-SE showed a strong band of 433 bp and a weak band of 582 bp reflecting the fact that overexpression of TβRII-SE downregulates TβRII isoform A expression. Similarly, when TβRIIA-DN was overexpressed in hASC cells, TβRII-SE expression (433 bp) could not be detected. Finally, in hASC cells transduced with the lentivector encoding only the eGFP marker gene, a weak band representing expression of TβRII-A was detected, suggesting that viral transduction "per se" downregulates TβRII expression.

mRNA levels of all three isoforms of Type II TGF-β receptor were also quantified by qRT-PCR (FIG. 13). It was found that in untransduced cells (UT), membrane bound TBRII-A and B variants were the main molecules to be expressed and TβRII-SE expression was minimal, as expected. Contrarily, when the new isoform expression was increased in hASC cells, both TβRII-A and B variants decreased dramatically, due to a compensation effect which shows the agonistic effect of the TβRII-SE isoform.

Figure 14:
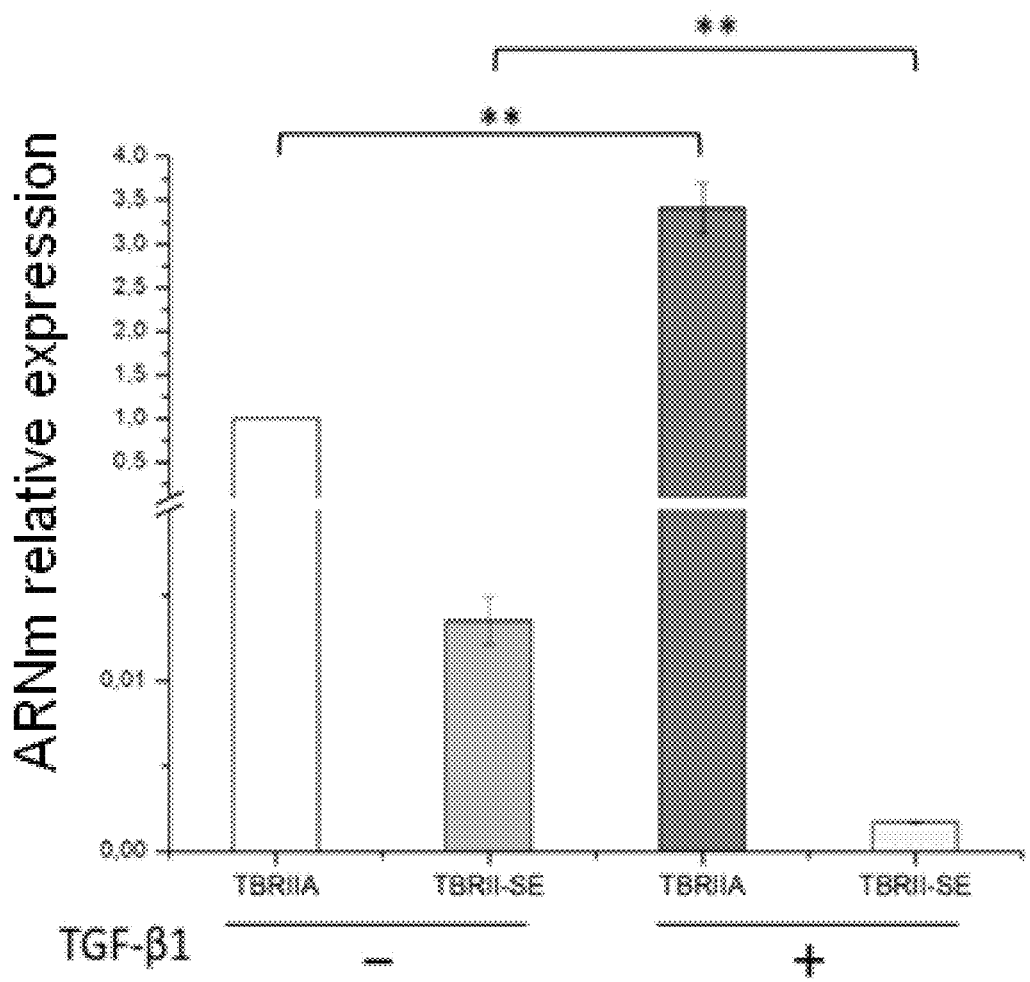
FIG. 14 shows mRNA levels of TβRII receptors in hASCs cells incubated with and without exogenous TGFβ-1.

This compensation effect was also verified by addition of exogenous TGF-β1 and analysis of mRNA levels of the TβRII variants in hASCs cells (FIG. 14). It was found that upon addition of TGF-β1, TβRII-A increased and TβRII-SE decreased compared to untreated cells, suggesting once again that the TβRII-SE isoform acts as a TGF-β1 agonist.

Figure 15:
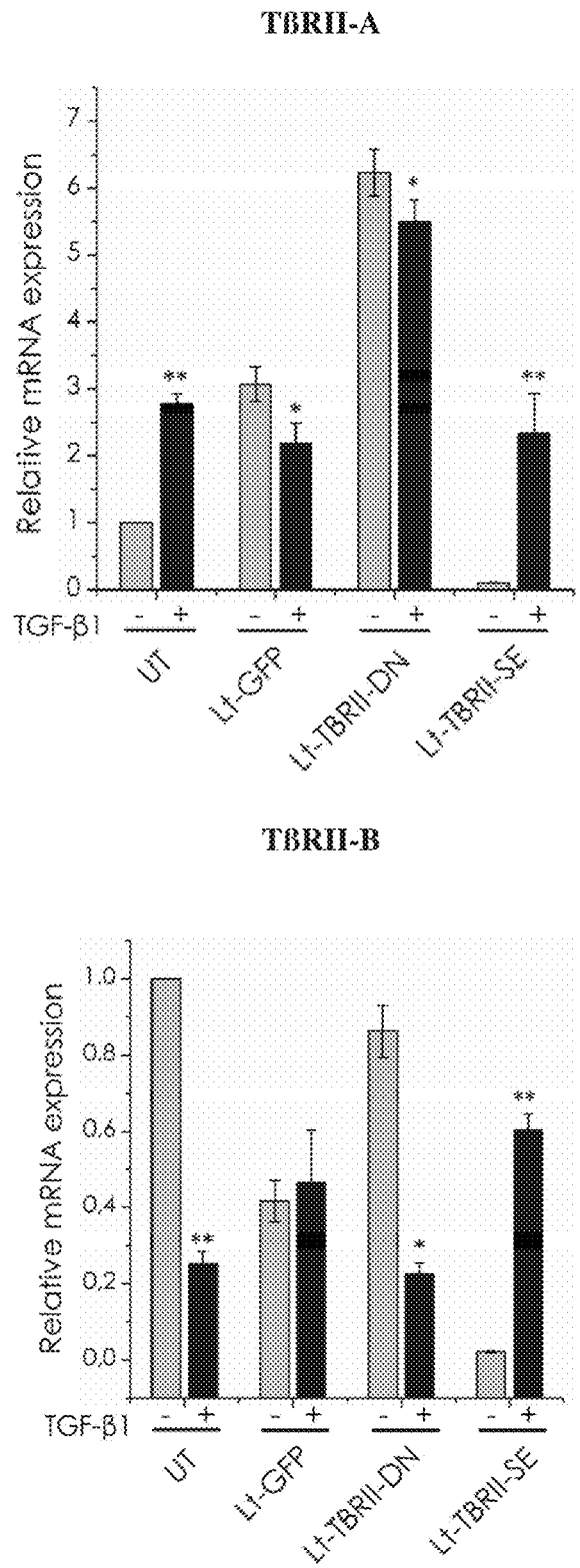
FIG. 15 shows mRNA levels of isoforms TβRII-A and TβRII-B in hASCs cells transduced with lentiviral vectors (Lt) encoding TβRII-SE and control vectors incubated with and without TGFβ-1.

According to this, it was also found that mRNA of both TβRII-A and TβRII-B are highly upregulated (40- and 50-fold increase, respectively) in cells overexpressing Lt-TβRII-SE in the presence of physiological concentrations of TGF-β1 compared to levels of mRNA produced in the absence of exogenous TGF-β1, further confirming the role of TβRII-SE acting as a TGF-β1 agonist by increasing the expression of membrane-bound receptors TβRII and TβRII-B (FIG. 15).

Figure 16:
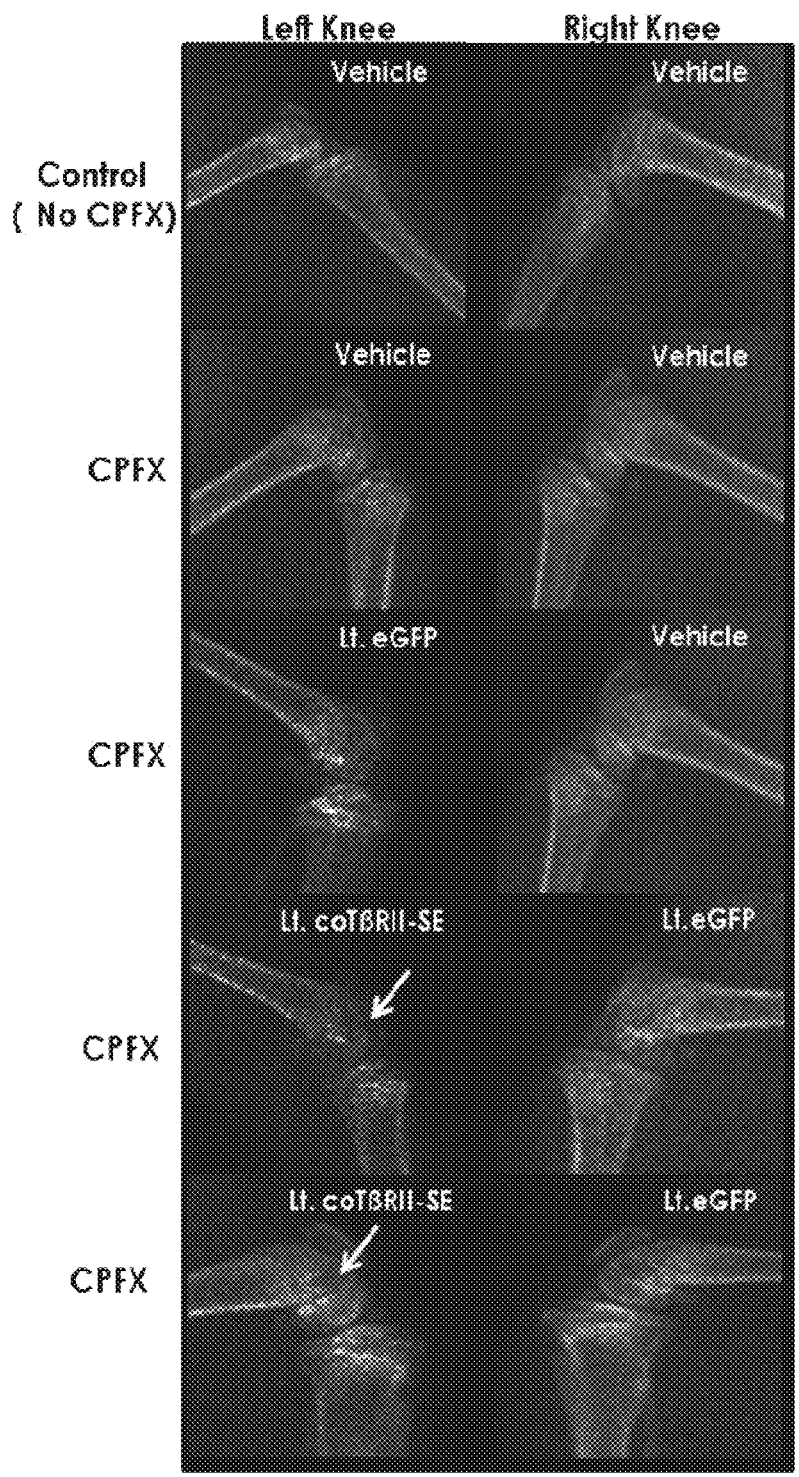
FIG. 16 shows X-ray images of rats treated with ciprofloxacin (CPFX) and intra-articularly injected in the knees with Lt.coTβRII-SE, Lt.eGFP, and culture medium (vehicle). White arrows indicate radiolucent images.

Furthermore, the effect of TβRII-SE recombinant isoform was measured on a panel of 80 cytokines secreted by hASCs cells (FIG. 16). Cells were transduced with either control Lt-GFP, the TGF-β1 inhibitor Lt. TβRII-DN, or Lt-TβRII-SE and incubated in the presence or absence of exogenous TGF-β1. Collected supernatants were used to analyze the cytokines in a Cytokine Array G5 (Raybiotech, Inc. Norcross, USA).

TABLE 2

| Autocrine TGF-β1 | | | | | |
|---|---|---|---|---|---|
| | DN | SE | | DN | SE |
| Hematopoietic cytokines | | | Insulin Like Growth Factor Superfamily | | |
| G-CSF | ↓ | ↓ | IGF-1 | ↓ | ↓ |
| M-CSF | ↑ | UC | IGFBP-1 | ↑ | UC |
| GM-CSF | ↑ | ↑ | IGFBP-3 | ↓ (15.60) | ↓ |
| IL-6* | UC | UC | IGFBP-4 | abs | abs |
| IL-7 | ↑ (2.02) | ↓ | Tumor Necrosis Factor Superfamily | | |
| LIF | UC | UC | TNF-α | ↑ (7.77) | ↓ |
| FLT3-L | UC | ↓ | TNF-β | UC | ↓ (1.85) |
| SCF | abs | abs | LIGHT | abs | abs |
| IL-3 | ↑ | UC | Fibroblast Growth Factor Family | | |
| Oncostatin M | UC | ↓ | FGF-7 | UC | ↓ |
| Angiogenic cytokines | | | FGF-9 | ↑ | UC |
| VEGF | ↑ (0.65) | ↓ (1.85) | Neurotrophins | | |
| Angiogenin | UC | UC | BDNF | ↑ | UC |
| HGF | ↓ (1.81) | ↑ (7.65) | NT-3 | ↑ | UC |
| EGF | abs | abs | NT-4 | UC | UC |
| PIGF | UC | ↓ | Tissue Inhibitor of Metalloproteinases Family | | |
| Chemokines | | | TIMP-1 | UC | UC |
| cxcl GRO | UC | UC | TIMP-2 | UC | UC |
| CXCL1 (GROα) | ↑ | UC | Macrophage Activating Factors | | |
| CXCL5 (ENA-78) | UC | ↑ (1.62) | INF-γ | UC | ↓ |
| CXCL6 (GCP-2) | UC | UC | MIF | UC | ↑ (1.97) |
| CXCL8 (IL-8) | UC | ↓ (1.67) | IL-2 | ↑ | UC |
| CXCL9 (MIG) | UC | UC | Bone Remodeling Cytokines | | |
| CXCL10 (IP-10) | UC | UC | Osteopontin | abs | abs |
| CXCL12 (SDF-1) | ↑ | UC | Osteoprotegerin | UC | UC |
| CXCL13 (BLC) | abs | abs | Hormones | | |
| ccl CCL1 (I-309) | ↑ | UC | Leptin | ↓ (1.79) | ↓ |
| CCL2 (MCP-1) | UC | UC | GDNF Family | | |
| CCL4 (MIP1b) | ↑ | UC | GDNF | UC | UC |
| CCL5 (RANTES) | ↓ (1.89) | ↓ (7.85) | Anti-inflammatory Interleukins | | |
| CCL7 (MCP-3) | UC | UC | IL-10 | ↑ | UC |
| CCL8 (MCP-2) | ↓ (3.60) | ↑ | IL-13 | ↓ (5.47) | ↓ |
| CCL11 (Eotaxin) | UC | ↓ (2.39) | Pro-inflammatory Interleukins* | | |
| CCL17 (TARC) | UC | UC | IL-1α | ↑ (3.11) | ↓ |
| CCL18 (PARC) | ↑ (3.46) | ↓ | IL-1β | abs | abs |
| CCL20 (MIP3a) | abs | abs | IL-5 | UC | ↓ (1.87) |
| CCL24 (Eotaxin-2) | ↓ | ↓ | IL-12 p70 | ↑ | UC |
| CCL26 (Eotaxin-3) | abs | abs | IL-15 | abs | abs |
| TGF-β Family | | | | | |
| TGF-β1 | ↑ (2.57) | ↑ (4.94) | | | |
| TGF-β2 | ↑ (1.61) | ↓ (1.55) | | | |

| Paracrine TGF-β1 (3 pg/μl) | | | | | |
|---|---|---|---|---|---|
| | DN | SE | | DN | SE |
| Hematopoietic cytokines | | | Insulin Like Growth Factor Superfamily | | |
| G-CSF | ↓ | ↓ | IGF-1 | abs | Abs |
| M-CSF | abs | abs | IGFBP-1 | abs | Abs |
| GM-CSF | ↑ (4.89) | ↓ | IGFBP-3 | ↓ | ↓ |
| IL-6* | UC | UC | IGFBP-4 | UC | ↑ |
| IL-7 | UC | ↓ | Tumor Necrosis Factor Superfamily | | |
| LIF | ↓ (2.43) | UC | TNF-α | UC | ↓ |
| FLT3-L | UC | UC | TNF-β | ↓ | ↓ |
| SCF | UC | UC | LIGHT | ↓ | ↓ |
| IL-3 | ↓ | ↓ | Fibroblast Growth Factor Family | | |
| Onc M | abs | abs | FGF-7 | abs | Abs |
| Angiogenic cytokines | | | FGF-9 | UC | UC |
| VEGF | ↓ (2.35) | UC | Neurotrophins | | |
| Angiogenin | ↓ (1.59) | UC | BDNF | abs | Abs |
| HGF | ↓ | ↑ (4.16) | NT-3 | ↓ | ↓ |
| EGF | ↓ | ↓ | NT-4 | abs | Abs |
| PIGF | ↓ | ↓ | Tissue Inhibitor of Metalloproteinases Family | | |
| Chemokines | | | TIMP-1 | ↑ (2.26) | UC |
| cxcl GRO | UC | UC | TIMP-2 | ↑ (2.07) | ↑ (1.52) |
| CXCL1 (GROα) | abs | abs | Macrophage Activating Factors | | |
| CXCL5 (ENA-78) | ↑ (1.64) | UC | INF-γ | ↓ | ↓ |
| CXCL6 (GCP-2) | ↑ (2.45) | ↓ | MIF | ↓ (1.76) | UC |
| CXCL8 (IL-8) | UC | ↓ (1.57) | IL-2 | abs | Abs |
| CXCL9 (MIG) | ↓ | ↓ | Bone Remodeling Cytokines | | |
| CXCL10 (IP-10) | ↓ | ↓ | Osteopontin | ↓ | ↓ |

TABLE 2-continued

| | | | | | | |
|---|---|---|---|---|---|---|
| | CXCL12 (SDF-1) | abs | abs | Osteoprotegerin | UC | ↓ (3.32) |
| | CXCL13 (BLC) | ↓ | ↓ | Hormones | | |
| ccl | CCL1 (I-309) | abs | abs | Leptin | ↓ (1.82) | ↓ (16.58) |
| | CCL2 (MCP-1) | UC | UC | GDNF Family | | |
| | CCL4 (MIP1b) | abs | abs | GDNF | abs | Abs |
| | CCL5 (RANTES) | ↓ (3.33) | ↓ (4.20) | Anti-inflammatory Interleukins | | |
| | CCL7 (MCP-3) | UC | ↑ (1.78) | IL-10 | ↑ (5.36) | ↓ |
| | CCL8 (MCP-2) | ↑ | UC | IL-13 | ↓ | ↓ |
| | CCL11 (Eotaxin) | UC | UC | Pro-inflammatory Interleukins* | | |
| | CCL17 (TARC) | UC | UC | IL-1α | ↓ | ↓ |
| | CCL18 (PARC) | ↓ | ↑ (3.38) | IL-1β | UC | UC |
| | CCL20 (MIP3a) | UC | UC | IL-5 | ↑ (5.61) | ↓ |
| | CCL24 (Eotaxin-2) | abs | abs | IL-12 p70 | ↓ | ↓ |
| | CCL26 (Eotaxin-3) | abs | abs | IL-15 | ↓ | ↓ |
| | TGF-β Family | | | | | |
| | TGF-β1 | UC | UC | | | |
| | TGF-β2 | UC | ↓ (2.27) | | | |

The results obtained with cytokine arrays are shown in Table 2. Increase or decrease of cytokines levels are referred to the levels secreted by cells transduced with the control vector Lt.eGFP either in the presence (paracrine) or absence (autocrine) of exogenous TGF-β1. UC: unchanged levels with respect to cells transduced with the control vector Lt.eGFP. Abs: absent in mock transducer cells control. Dark grey boxes: decreased to undetected levels or absent in the supernatant of cells transduced with control vector Lt.eGFP.

Light gray boxes: cytokines present.

It is shown that in ASC cells overexpressing TβRII-DN with a high TGF-β1 concentration, OPG secretion remains unchanged with respect to the values obtained in Lt.eGFP-transduced control cells, making cells insensitive to TGF-β1.

On the other hand, high TGF-β1 concentrations caused a dramatic drop of OPG secretion in TβRII-SE overexpressing cells compared to control cells (Lt.eGFP-transduced). The TβRII-SE isoform acts oppositely to the TGF-β1 inhibitor (TβRII-DN) and seems to favor osteoclastogenesis.

Table 3 summarizes the results obtained by other authors, and those compared to the results disclosed in the present application regarding the cytokine array and the relationship with osteoarthritis (OA).

| MSC/ Osteoblasts | Disease | Bone/cartilage remodeling | Results of the Invention |
|---|---|---|---|
| High TGF-β1 | OA | Bone loss/increase of osteoclastic resorption Increased PTG content High angiogenesis Osteophyte outgrowth | Lower OPG TGF-β1 agonist Higher HGF TGF-β1 agonist |
| TGF-β1 inhibition (TβRII-DN) | OA-like | Decreased osteoclastic resorption Decreased PTG content/ increased cartilage loss Angiogenesis Decreased osteophyte formation | Higher OPG TGF-β1 antagonist No HGF TGF-β1 antagonist |

It is shown that in cells overexpressing TβRII-SE HGF secretion is highly upregulated both in the presence (4.16 times) or absence (7.65 times) of exogenous TGF-β1, whereas in cells overexpressing the dominant negative mutant TβRII-DN, HGF secretion decreases 1.81 times or is absent, in the absence and presence of exogenous TGF-β1, respectively. These results show that the TβRII-SE isoform is involved in the positive regulation of HGF.

Increased TGF-β1 acts differently in animals depending on whether injections were applied in normal or osteoarthritic models. In normal animals, either TGF-β1 protein or adenovirus TGF-β1 injection generates increased synthesis and content of proteoglycan and osteophyte formation. On the other hand, in osteoarthritis (OA)-induced models, increases in the TGF pathway help to decrease cartilage damage, proteoglycan and osteophyte formation. Thus, the effect of the TβII-SE isoform was analyzed either in CPFX-treated juvenile rats (24 days old) or untreated rats, by intra-articular injections of lentiviral vectors encoding a recombinant protein of the codon-optimized (co) TβRII-SE fused to the constant fragment (Fc) of the human immunoglobulin 1 (IgG1) (Lt.coTβRII-SE/Fc) or the enhanced green fluorescent protein (Lt.eGFP).

Seven days after injecting the vector into rats treated with ciprofloxacin (CPFX), only articulations overexpressing the fusion peptide or a fused coTβRII-SE/Fc isoform showed radiolucent images with irregular borders in the femoral condyle, consistent with intraosteal geodes (FIG. 16). It is shown that coTβRII.SE/Fc could cause osteolytic damage by bone resorption.

Figure 17:
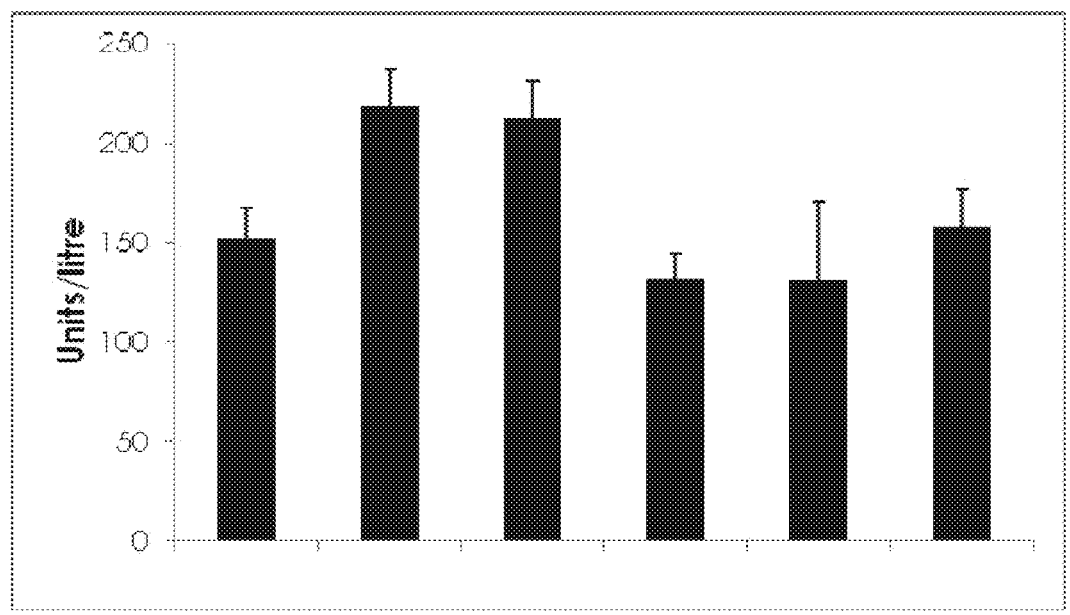
FIG. 17 shows a graphic of serum level measurements for aspartate transaminase (AST), in the same animals.

When compared to serum levels of urea, creatinine, total proteins, albumin, alkaline phosphatase, alanine transaminase (ALT), and aspartate transaminase (AST), a statistically significant difference was only found for the latter. An increase in aspartate transaminase (AST) was only observed in serum of rats treated with CPFX and intra-articularly injected with Lt.coTβRII-SE (FIG. 17). Mitochondrial and cytoplasmic forms of AST are found in all cells, so the increase of AST which was only observed in rats injected with Lt.coTβRII-SE/Fc in combination with CPFX show that coTβRII-SE enhance the effect of CPFX on tissue damage in muscle, tendons or other tissues.

Figure 18:
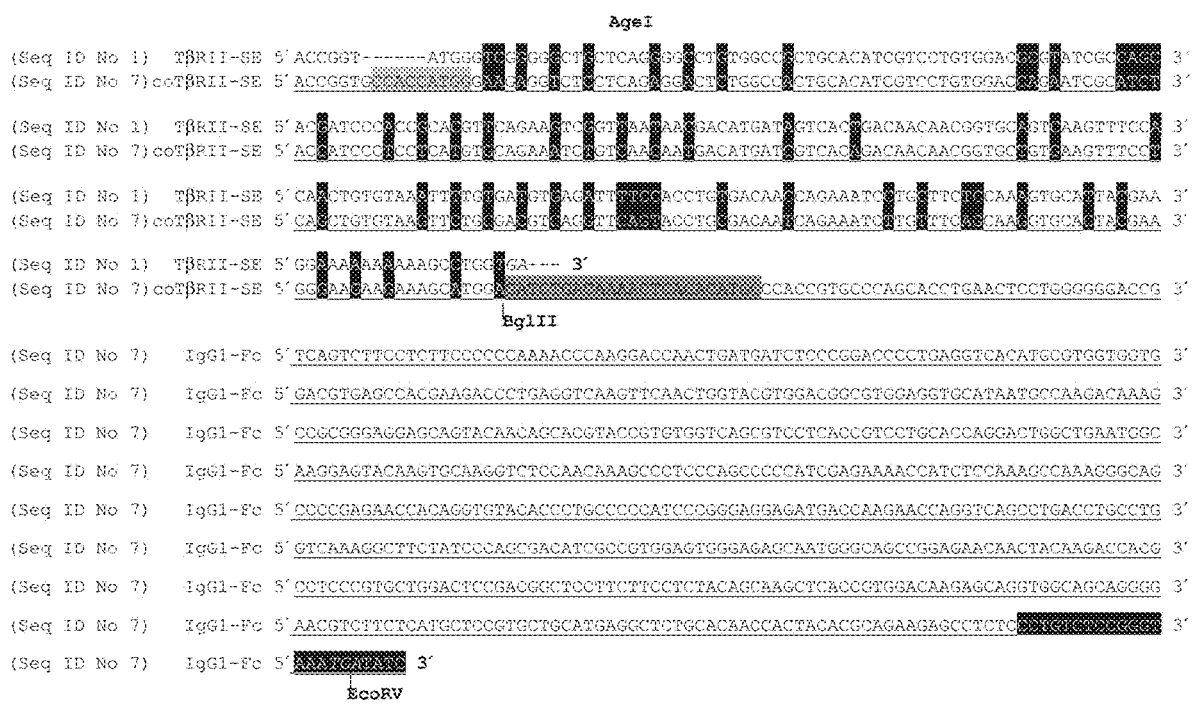
FIG. 18 shows a cDNA alignment to compare changes made to the recombinant TβRII-SE. To obtain coTβRII-SE/Fc (underlined sequence), a Kozak sequence (light gray box) was included in the TβRII-SE cDNA, to make translation initiation more efficient. Additionally, some nucleotides have been changed (black boxes with white letters) for codon optimization, to make translation more efficient in human cells. To allow fusion in frame of cDNA with the human IgG-Fc domain cDNA, the stop codon of TβRII-SE was removed (italics) and replaced by a BgIII recognition sequence in the new construct. Primers used for PCR-amplification of human IgG1 Fc coding sequences are shown in dark gray boxes.

In the present application, the generation of a new recombinant TβRII-SE protein expressed in human cells is shown. It is known that in nature, the concentration of soluble receptors is very low, thus, to increase the levels of the recombinant TβRII-SE protein, the original coding sequence was codon optimized, and a Kozak sequence was included (Epoch Biolabs Inc., Texas, USA) referred to herein as coTβRII-SE (SEQ ID No. 4) and encoded by SEQ ID No. 5 (FIG. 18). Additionally, to make the protein more stable in vivo, and for a more effective purification, the human IgG1 Fc region was cloned "in frame" downstream of the coding sequence of coTβRII-SE to obtain the fusion peptide coTβRII-Se/Fc, as previously mentioned (SEQ ID No. 6), encoded by SEQ ID No. 7 (FIGS. 18 and 19).

As can be observed, FIG. 18 shows a cDNA alignment to compare changes made to the recombinant TβRII-SE. To obtain the coTβRII-SE/Fc (underlined sequence), a Kozak sequence (light gray box) was included in the TβRII-SE cDNA, to make the initiation of translation more efficient. Additionally, some nucleotides have been changed (black boxes and white letters) for codon optimization, in order to make translation more efficient. To allow fusion in frame of cDNA with the human IgG-Fc domain cDNA, the stop codon of TβRII-SE was removed (italics) and replaced by a BglII recognition sequence in the new construct. Primers used for PCR-amplification of human IgG1 Fc coding sequences are shown in dark gray boxes.

As can be observed, FIG. 19 shows a protein alignment and allows for comparing changes made to the recombinant TβRII-SE. coTβRII-Se was fused "in frame" to the human IgG1 Fc domain. Asterisk: Stop Codon; Black Box: linker aminoacids; Grey box: Fc domain.

Figure 20:
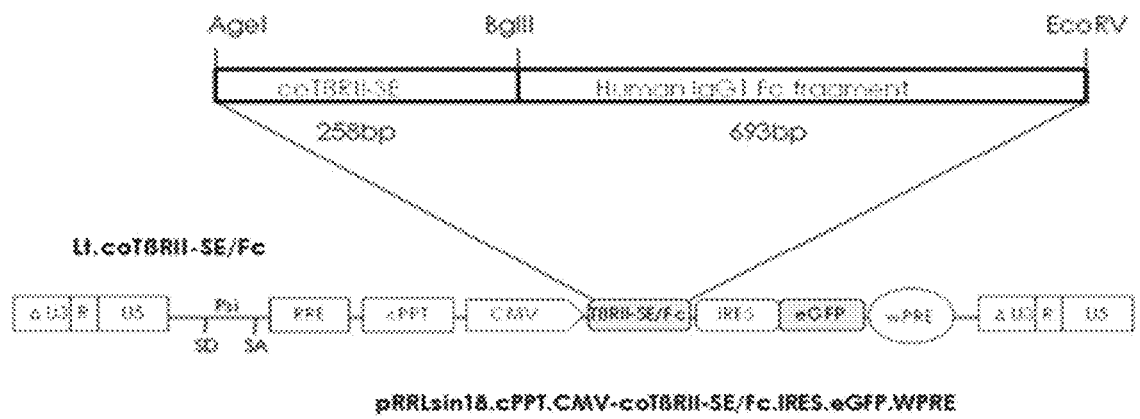
FIG. 20 shows a schematic diagram of the self-inactivating (SIN) bicistronic lentiviral vector encoding the fusion cassette coTβRII-SE/Fc together with ires eGFP, under the control of an internal CMV promoter.
Figure 21:
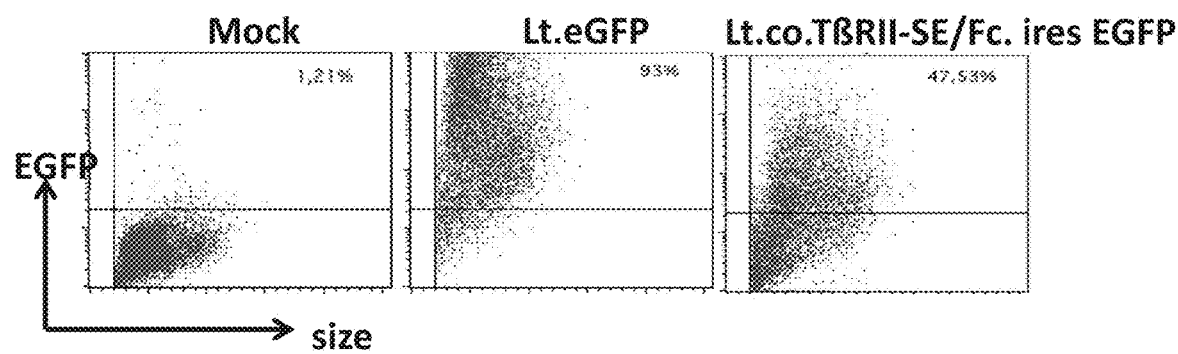
FIG. 21 shows flow cytometry dot plots demonstrating the efficiency of vector transduction of Lt.coTβRII-SE/Fc.ires eGFP and the control vector Lt. eGFP.
Figure 22:
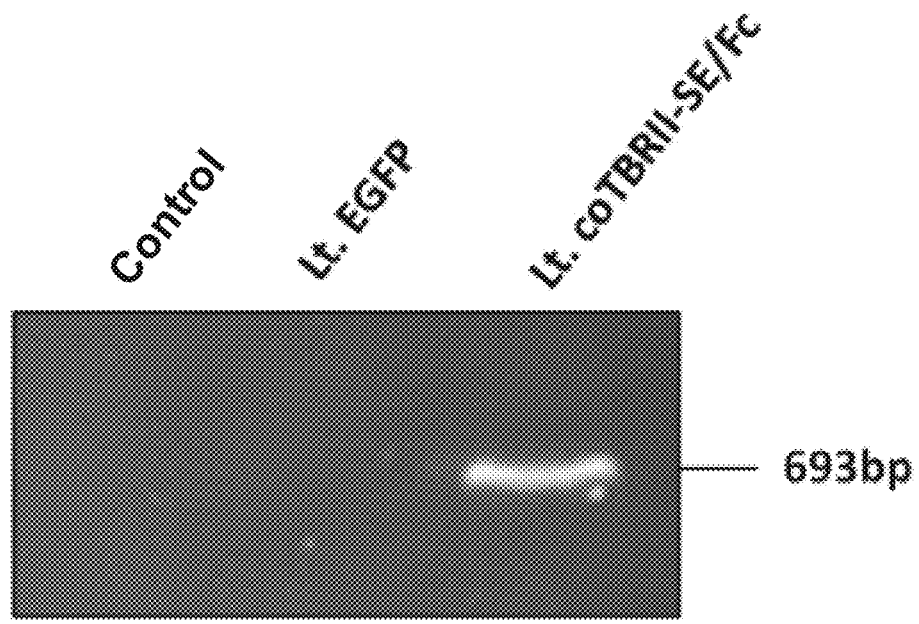
FIG. 22 shows the results of an agarose gel electrophoresis with RT-PCR products, using primers for amplifying IgG1 Fc, from RNAm of Mock, Lt.eGFP, and Lt. coTβRII-SE/Fc transduced A549 cells.
Figure 23:
FIG. 23 shows the results of a Western blot of cell lysates (CL) and supernatants (SN) from proteins of Mock, Lt.eGFP and Lt. coTβRII-SE/Fc transduced A549 cells.
Figure 24:
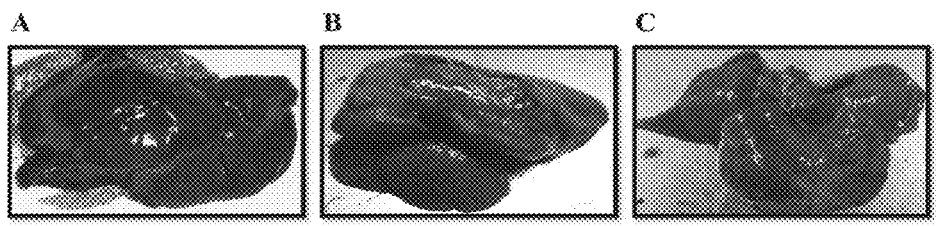
FIG. 24 shows the effect of TβRII-SE/Fc overexpression on gross appearance of livers in $CCl_4$-induced liver fibrosis in rats. Representative images of livers corresponding to animals treated with vehicle (A), $CCl_4$ (B) or Lv.TβRII-SE/Fc+$CCl_4$ (C).
Figure 26:
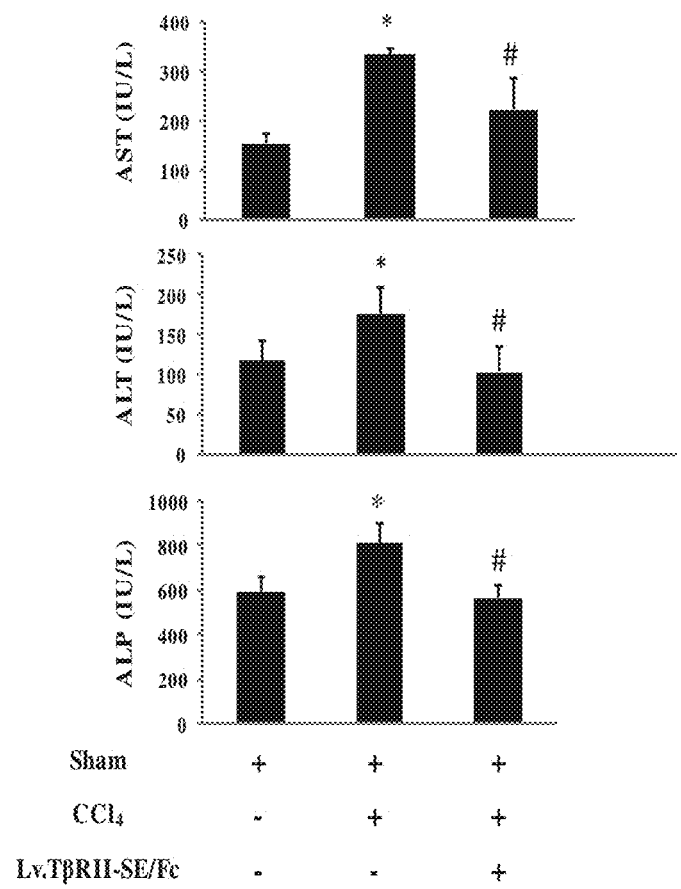
FIG. 26 shows the effect of TβRII-SE/Fc overexpression on serum liver enzymes in $CCl_4$-induced liver fibrosis in rats. Activity levels of serum liver enzymes in the different experimental groups: A) AST, B) ALT, C) ALP. Results are expressed as IU/L. *p<0.05: Vehicle vs $CCl_4$; #p<0.05: $CCl_4$ vs Lv.TβRII-SE/Fc+$CCl_4$. AST: Aspartate aminotransferase. ALT: Alanine aminotransferase. ALP: Alkaline Phosphatase. IU: International units.
Figure 27:
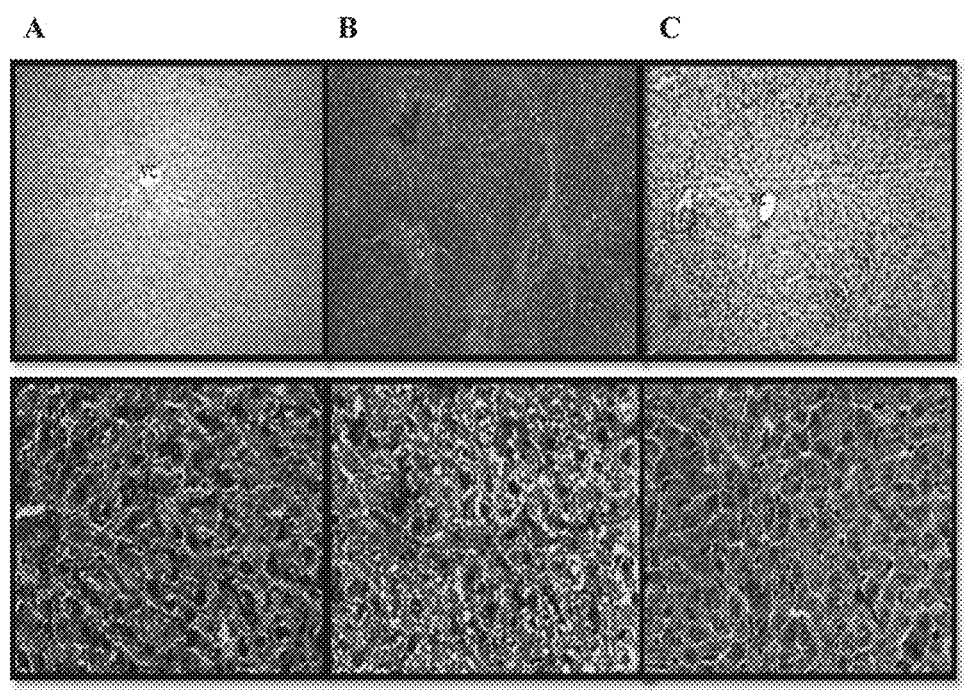
FIG. 27 shows the effect of TβRII-SE/Fc overexpression on liver histology. H&E staining. Representative images of liver histological sections stained with H&E of animals treated with vehicle (A), $CCl_4$ (B) or Lv.TβRII-SE/Fc+$CCl_4$ (C). Magnification 100× (upper panel) y 400× (lower panel).
Figure 28:
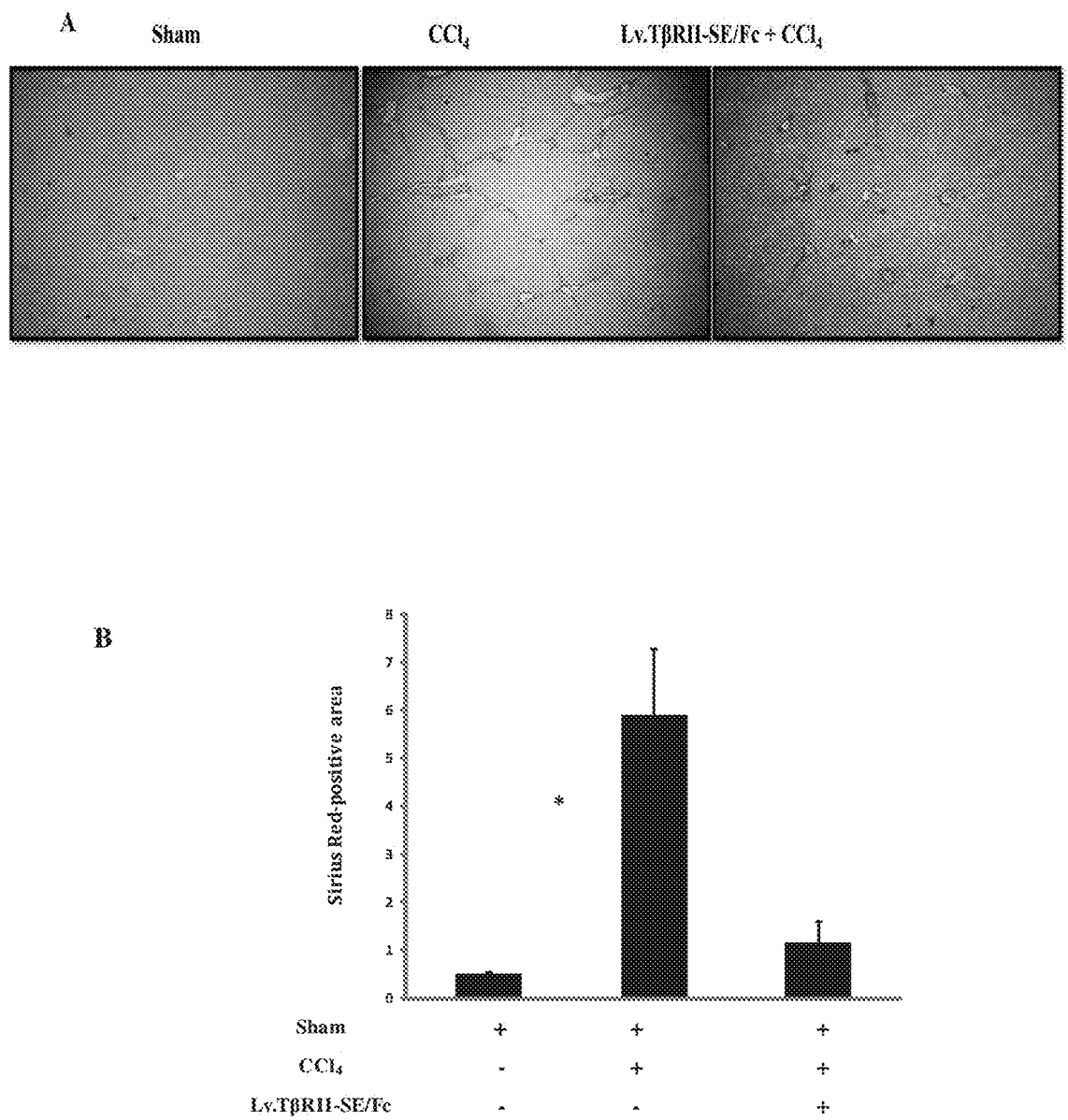
FIG. 28 shows the effect of TβRII-SE/Fc overexpression on liver histology by Sirius Red staining. A) Representative images of liver histological sections stained with Sirius Red of animals treated with vehicle (A), $CCl_4$ (B) or Lv.TβRII-SE/Fc+$CCl_4$ (C). Magnification 40×. B) Quantification of liver fibrosis. Results are expressed as mean percentage (%) of Sirius Red-positive area. *p<0.05: Vehicle vs $CCl_4$; #p<0.05: $CCl_4$ vs Lv.TβRII-SE/Fc+$CCl_4$.
Figure 29:
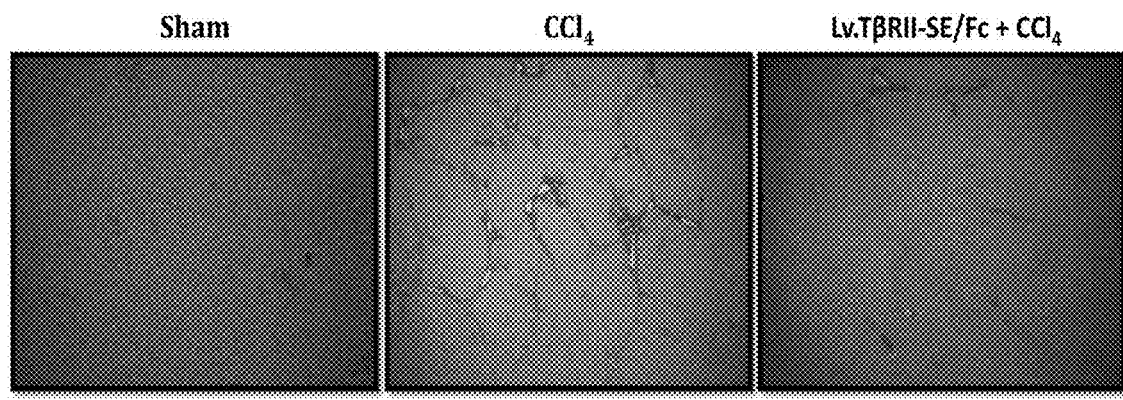
FIG. 29 shows the effect of TβRII-SE/Fc overexpression on HSC activation. Representative images showing α-SMA-positive areas in liver histological sections from animals treated with vehicle (A), $CCl_4$ (B) or Lv.TβRII-SE/Fc+$CCl_4$ (C). Magnification 40×.
Figure 30:
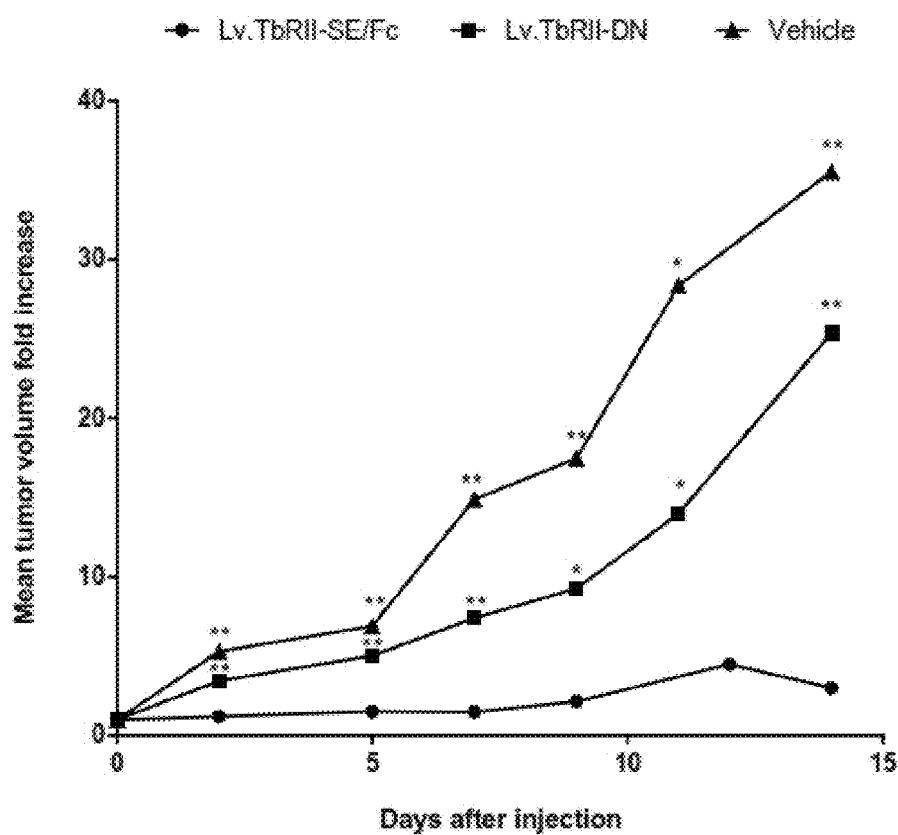
FIG. 30 shows the effect of TβRII-SE/Fc overexpression on tumor growth in vivo. Increased volumen of subcutaneous TN60 mammary carcinoma in syngenic CH3 mice after intratumoral injection with the lentiviral vector of the invention, ($1.5 \times 10^6$ tranduction units/tumor) encoding the recombinant fusion protein TβRII-SE/Fc (Lv.TβRII-SE/Fc) (N=7) (circles); the dominant negative mutant TβRII-DN (Lv.TβRII-DN) (N=6) (squares); and vehicle (cell culture medium) (N=6) (triangels). *p<0.05; **p<0.01.
Figure 31:
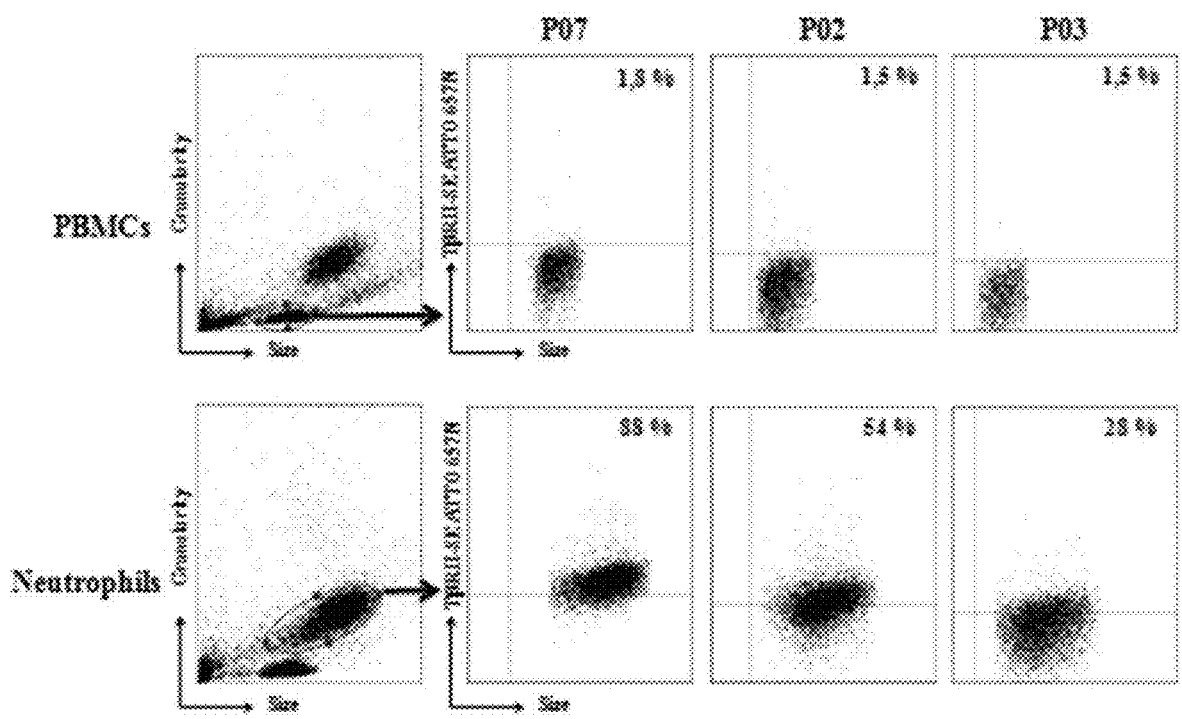
FIG. 31 shows flow cytometry evaluation of intracellular TβRII-SE in neutrophils from Rheumatoid Arthritis (AR) patients. Flow cytometry plots of lymphocytes (Top Panel) and neutrophils (Bottom Panel) from patients with low (P07), moderate (P02) and high (P03) disease activity, where TβRII-SE was detected by using the anti-TβRII-SE monoclonal antibody of the invention conjugated with ATTO647N. Left Panel shows lymphocytes from PBMC (Top) and neutrophils (bottom) taken to analyze the percentage of cells expressing TβRII-SE.

Subsequently, the recombinant coTβRII-SE/Fc cDNA was inserted between the AgeI and EcoRV sites of a SIN lentiviral vector (FIG. 20).

Figure 32:
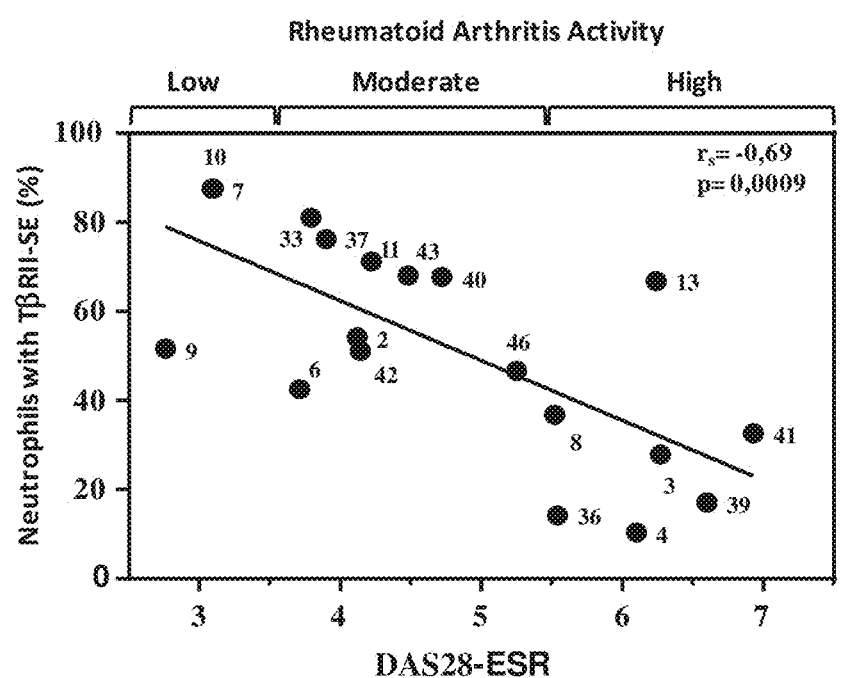
FIG. 32 shows the correlation analysis between the percentage of neutrophils evaluated by flow cytometry from 19 AR patients expressing TβRII-SE, and AR disease activity measured by DAS28-ESR (Disease Activity Score—erythrosedimentation rate) of the same patients. $r_s$=Spearman's rank correlation coefficient.

To check recombinant protein production, A549 cells were transduced at an MOI=300 either with the control vector Lt.eGFP (93% of eGFP expressing cells) or Lt.coTβRII.SE/Fc (47.53% of eGFP expressing cells) and Mock transduced (FIG. 21).

To verify the presence of human IgG1 mRNA in Lt.coTβRII-SE/Fc transduced cells, total mRNA of Mock transduced (vehicle), Lt.eGFP transduced and Lt.coTβRII-SE/Fc transduced cells was extracted and RT-PCR assays were performed using specific primers for human IgG1-Fc (FIG. 22). As expected, human IgG1 Fc domain mRNA was only detected in Lt.coTβRII-SE/Fc transduced A549 cells.

Additionally, to verify the presence of the TβRII-SE/Fc protein both in cell lysates and supernatants, total proteins from Mock, Lt.eGFP and Lt.coTβRII-SE/Fc transduced cells lysates and supernatants were western blotted (FIG. 23) using a monoclonal antibody, capable of specifically detecting TβRII-SE. In this way, a predicted protein of circa 50 kD could be detected, which included 18 kD of TβRII-SE plus 35 kD of the human IgG1 Fc domain, both in cell supernatants and lysates of Lt.coTβRII-SE/Fc-transduced cells only.

A method to treat liver fibrosis was developed employing the lentiviral vector encoding the fusion protein TβRII-SE/Fc of the invention.

To study the effect of TβRII-SE/Fc expression on liver fibrogenesis, a rat model of carbon tetrachloride (CCL4) induced liver fibrosis was used. After animal euthanasia, liver gross appearance was evaluated macroscopically. FIG. 24 shows that livers from group I (vehicle), exhibited a reddish color, a smooth lustrous surface, and a regular shape. As it was expected, in $CCl_4$-treated animals livers looked shrunken with irregular shape, an opaque color, and an unsmooth surface. Rat livers of the Lv.TβRII-SE/Fc+$CCl_4$ group had a more regular shape, were redder and their surfaces were smoother than liver surfaces of the $CCl_4$-group. These results suggest a beneficial effect of TβRII-SE/Fc expression at macroscopic level against $CCl_4$-induced fibrosis in rats.

Effect of TβRII-SE/Fc expression on body weight and liver to body weight ratio: body weight was controlled in all rats throughout the experiment. It was observed that $CCl_4$ treatment during eight weeks caused a growth retardation of rats, evidenced by the decrease of final body weight gain compared to rats of the vehicle group. Injection of Lv.TβRII-SE/Fc partially reversed the BW loss induced by this hepatotoxic agent. This beneficial effect was more evident after 4 weeks of $CCl_4$ administration (FIG. 25A). In addition, $CCl_4$ administration induced an increase in the LW/BW ratio respect to the rats of the control group injected only with vehicle, suggesting liver injury and extracellular matrix protein accumulation. Injection of Lv.TβRII-SE/Fc prior to the treatment with $CCl_4$ led to a LW/BW ratio comparable to that found in the Vehicle group of rats, suggesting a beneficial effect of TβRII-SE/FC expression against liver injury induced by $CCl_4$ (FIG. 25B).

Effect of TβRII-SE/Fc expression on serum liver enzymes: to evaluate liver injury, AST and ALT serum levels were determined. As it is shown in FIGS. 26A and B, $CCl_4$ administration significantly increased both transaminase levels respect to those found in the Vehicle group of rats. Conversely, injection of Lv.TβRII-SE/Fc induced a significant decrease in AST and ALT levels. On the other hand, ALP showed increased response to $CCl_4$ administration, which was reversed as a result of the Lv.TβRII-SE/Fc injection (FIG. 26C). These data suggest that TβRII-SE/Fc expression exerts a beneficial effect against liver injury induced by $CCl_4$.

Effect of TβRII-SE/Fc expression on liver architecture: histological sections were stained with H&E to evaluate the general architecture of the liver. This analysis revealed that animals that received vehicle instead of $CCl_4$, presented livers with a conserved architecture with cords of hepatocytes radiating from central veins (FIG. 27A). Conversely, $CCl_4$ administration during 8 weeks led to a disrupted liver architecture, extensive liver injury and prominent fibrosis (FIG. 27B). These detrimental effects were clearly attenuated when animals were injected with Lv.TβRII-SE/Fc before the treatment with $CCl_4$ (FIG. 27C).

Effect of TβRII-SE expression on liver fibrosis: collagen deposition was evaluated by Sirius Red staining in liver sections from different experimental group rats. $CCl_4$ administration induced extensive deposition of collagen fibers evidenced by the observation of bridging fibrosis. FIG. 28A shows that Injection of Lv.TβRII-SE/Fc reduced liver fibrosis induced by $CCl_4$ (FIG. 28A). Quantification of Sirius Red-positive areas (SR+) demonstrated a significant increase in collagen deposition in the $CCl_4$ group compared to the Vehicle group. However, Lv.TβRII-SE/Fc administration significantly reduced SR+ areas, with reference to the $CCl_4$ group (FIG. 28B). Moreover, α-SMA expression, a known marker of hepatic stellate cell (HSC) activation, was evaluated by immunohistochemistry. In comparison to rats only injected with vehicle, $CCl_4$ treated animals showed a prominent increase of α-SMA-positive areas. However, HSC activation was markedly reduced in $CCl_4$ rats treated with Lv.TβRII-SE/Fc (FIG. 29). These data demonstrates that TβRII-SE/Fc expression reduces HSC activation, decreases pathological collagen fiber deposition, and limits liver injury induced by $CCl_4$.

Use of the Lv.TβRII-SE/Fc vector to treat cancer: it was observed that intratumoral TβRII-SE/Fc overexpression inhibits tumor growth (FIG. 30), compare to controls.

Assays were conducted to determine rheumatoid arthritis (RA) disease activity by means of measuring TβRII-SE by flow cytometry, with the TβRII-SE monoclonal antibody of the invention, conjugated with ATTO647N. The percentage of neutrophils expressing TβRII-SE (FIG. 31, bottom panel) was quantified taking as basal reference the highest TβRII-SE ATTO647N fluorescence value in the lymphocyte population of each patient. (FIG. 31, top panel).

When the percentage of neutrophils expressing TβRII-SE of each patient was correlated with its matching disease activity score (DAS28-ESR) value, it could be observed a negative correlation (Spearman's rank correlation coefficient $r_s=-0.69$), statistically significant (p=0.0009), (FIG. 32). These data suggested variation in the levels of this isoform in RA patients. In this sense, TβRII-SE might be used as a therapeutic target. Also, the results give evidence that the evaluation of TβRII-SE in neutrophils might represent an alternative assay to determine RA disease activity in patients.

Also, experiments were carry out to detect intracellular TβRII-SE concentration by In-cell ELISA in neutrophils from patients (N=5) with different RA activity levels. (Table 4).

TABLE 4

| Patient ID Number | Relative TβRII-SE levels |
|---|---|
| 9 | 16.48 |
| 10 | 15.98 |
| 11 | 20.69 |
| 12 | 10.26 |
| 13 | 5 |

Relative intracellular TβRII-SE protein levels in neutrophils from RA patients were correlated with their matching DAS28-ESR score (Table 5).

TABLE 5

| Patient ID Number | Relative TβRII-SE levels |
|---|---|
| 9 | 2.76 |
| 10 | 3.09 |
| 11 | 4.22 |
| 12 | 4.31 |
| 13 | 6.24 |

Figure 33:
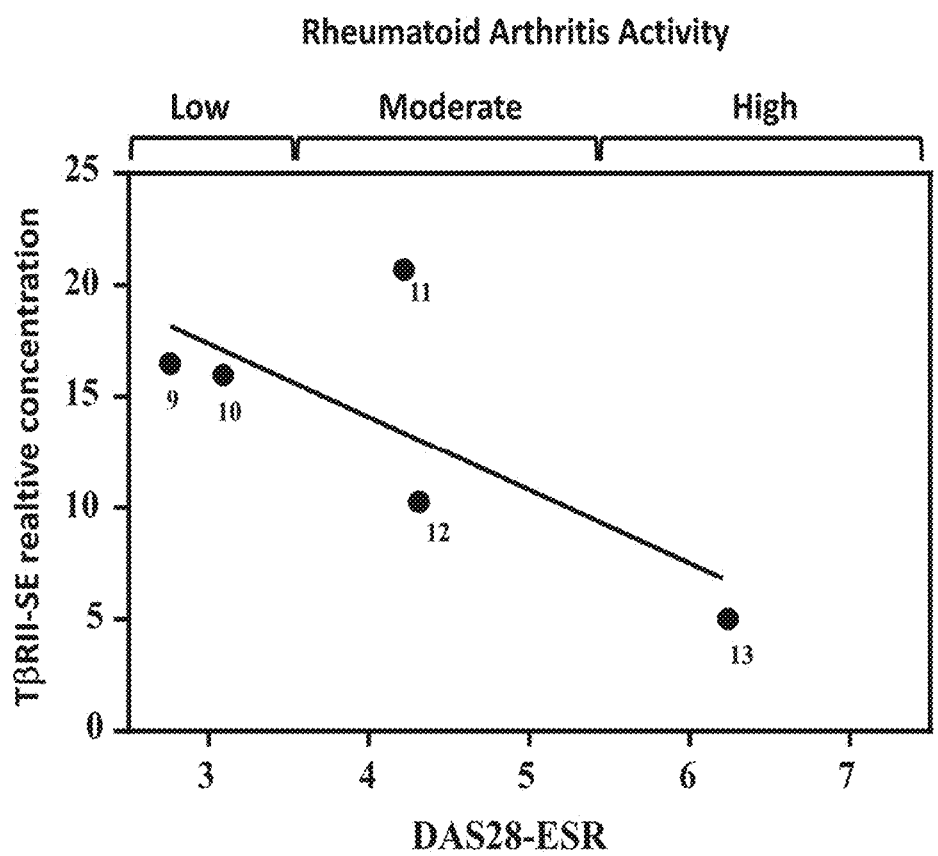
FIG. 33 shows the correlation analysis between TβRII-SE protein levels in peripheral blood plastic adherent cells from 5 patients evaluated by In-cell ELISA, and DAS28-ESR of the same patients. $r_s$=Spearman's rank correlation coefficient.

When both sets of data were analyzed by the Spearman's Rank correlation test, a negative correlation was observed between TβRII-SE levels and DAS28-ESR (FIG. 33), where TβRII-SE levels decreases while DAS28-ESR score increases (Disease activity: (Low=2.4<DAS28 3.6, moderate= 3.6<DAS28 5.5, High=DAS28>5.5 (2).

This invention is better illustrated in the following examples, which should not be construed as limiting the scope thereof. On the contrary, it should be clearly understood that other embodiments, modifications and equivalents thereof may be possible after reading the present description, which may be suggested to a person of skill without departing from the spirit of the present invention and/or the scope of the appended claims.

EXAMPLES

Example 1: Isolation, Cloning and Sequencing of the TβRII-SE Isoform

Human adipose derived mesenchymal stromal cells (hASC) were obtained from 20 g subcutaneous fat following the protocol described by Zuk et al. (Zuk P A, et al. *Mol Biol Cell* 13: 4279-95, 2002) and cultured in the presence of DMEM supplemented with 10% human serum and 1% L-glutamine. Epstein Barr Virus immortalized lymphoblastoid cells were generated from peripheral blood mononuclear cells as described (Protocols in Immunology) and cultured with RPMI medium. Human A459 (lung adenocarcinoma), HT1080 (fibrosarcoma), Caco-2 (colorectal carcinoma), Hep 3B (hepatocellular carcinoma), Jurkat (acute lymphoblastoid leukemia), HEK293 (human embryonic kydney), and 293T cell lines were cultured in DMEM supplemented with 10% FCS and 1% penicillin/streptomycin. The cells were cultured in a humidified 5% $CO_2$ incubator at 37° C.

Purification of Different Leukocyte Subpopulations

Granulocytes, lymphocytes and monocytes were isolated from heparinized peripheral blood by Ficoll-Paque™ PLUS (GE Healthcare Bio-Sciences AB) gradient centrifugation. After centrifugation two fractions were obtained, one containing granulocytes/erythrocytes and another with peripheral blood mononuclear cells (PBMC). To obtain granulocytes, erythrocytes were lysed with KCl 0.6 M. PBMCs were labelled with anti $CD3^+$, $CD14^+$, and $CD19^+$ monoclonal antibodies conjugated with magnetic microbeads (Miltenyi Biotech) and separated using MS columns (Miltenyi Biotech) in a MiniMACS magnet (Miltenyi Biotech). Viable cells were determined by Trypan blue dye exclusion and counted in an hemocytometer. The purity of B- and T-lymphocyte and monocyte sub-populations was determined by flow cytometric analysis using a FACSCalibur flow cytometer (BD Biosciences). Cell sub-populations homogenized in RNA Lysis Buffer (SV Total RNA Isolation System, Promega) were stored at −80° C. until RNA extraction.

Cloning and Sequencing of PCR Fragments

TβRII PCR fragments were cloned by insertion into the pGEM-T Easy plasmid (Promega Corporation WI, USA) under the conditions established by the manufacturers and *E. coli* transformation:1 pH PCR fragments were sequenced by using M13 forward and direct primers in a DNA sequencer ABI 3130 (Applied Biosystems Inc, CA, USA).

Example 2: Cloning of the Codon Optimized (Co) TβRII-SE/Fc Isoform Fusion Construct The TβRII-SE coding sequence containing an AgeI site was codon optimized, the stop codon was deleted and a Kozak sequence included (Epoch Biolabs Inc. Texas, USA). The human IgG1 Fc coding sequence was obtained by RT-PCR from total blood mRNA using specific oligonucleotides as primers (forward: 5'AGA TCT GAC AAA ACT CAC ACA TGC 3' (SEQ ID No. 8) and reverse: 5' GAT ATC TTT ACC CGG AGA CAG G 3' (SEQ ID No. 9)), containing a BgIII site (forward primer) and EcoRV (reverse primer), to allow in frame fusion to TβRII-SE and to the lentiviral vector, respectively. The fusion construct (coTβRII-SE/Fc) of 951 bp AgeI/EcoRV comprises 258 bp of the coTβRII-SE fused in frame with 693 bp of the human IgG1-Fc.

Example 3: Lentiviral Vectors

The cDNA encoding the three human TβRII isoforms were cloned into the pRRLsin18.cPPT.WPRE lentiviral vector, generating the transfer vectors pRRLsin18.cPPT.CMV-TβRII-SE.ireseGFP.WPRE, pRRLsin18.cPPT.CMV-TβRII-DN.ireseGFP.WPRE, and pRRLsin18.cPPT.CMV-coTβRII-SE/Fc.ireseGFP.WPRE. Vesicular Stomatitis Virus G protein-pseudotyped lentiviruses (VSV-G) were generated by transient transfection of the transfer vectors together with the envelope plasmid (pCMV-VSVG), the packaging plasmid (pMDLg/pRRE) and Rev plasmid (pRSV-REV), into the 293T cell line, as previously described (R. A. Dewey, et al. *Experimental Hematology* 34: 1163-1171, 2006). The supernatant was harvested once every 12 hours for 48 hours and frozen in aliquots. Viral titers were determined by transducing A549 cells (yielding $10^7$ infectious particles per milliliter). The pRRLsin18.cPPT.CMV-eGFP.WPRE lentiviral vector was used as control.

Example 4: RT-PCR and RT-qPCR

Total RNA from different primary cultures and cell lines was isolated using the Absolutely RNA kit (Stratagene, La Jolla, Calif., USA). First-strand cDNA was synthesized by mixing 1 µg of DNA free total RNA, 50 pmol primer p(DT)15 (Roche Diagnostics GmbH, Mannheim, Germany), 0.5 mM deoxyribonucleotide triphosphate, 5 mM dithiothreitol, and 1 U Expand Reverse Transcriptase (Roche Diagnostics GmbH). cDNA corresponding to different isoforms of TβRII receptor was detected by PCR amplification in the presence of Expand High Fidelity polymerase (Roche Diagnostics GmbH), 0.2 mM dNTPS, and 0.5 µM of each primer (forward: 5'ACCGGTATGGGTCGGGGGC TGCTC3' (SEQ ID No. 10) and reverse: 5'GTCGACTCAGTAG CAGTAGAAGATG3' (SEQ ID No. 11) for 35 cycles using the following PCR conditions: 1 min. at 95° C., 1 min. at 55° C., and 1 min. at 95° C.

Quantitative RT-PCR was performed on diluted cDNA samples with FastStart Universal SYBR Green Master (Rox) (Roche Applied Science) using the Mx3005P™ Real-Time PCR Systems (Stratagene) under universal cycling conditions (95° C. for 10 min; 40 cycles of 95° C. for 15 s; then 60° C. for 1 min). All results were normalized to GAPDH mRNA levels and further the results were analyzed using the MxPro™ QPCR computer program and Infostat statistical computer program (Di Rienzo J. A., et al. InfoStet version 2010. Grupo InfoStet, FCA, National University of Cordoba, Argentina. URL, http://www.infostat.com.ar)

Example 5: In Vitro Bioassay for the TβRII-SE Isoform and Other Isoforms Using the MTT Proliferation Assay A549 cells were transduced with lentiviral vectors at a multiplicity of infection (MOI) of 50 in the presence of 8 µg/ml polybrene. Percentage of eGFP positive cells was measured in a FACscalibur (Becton Dikinson) cytometer.

Cells were harvested, counted, and inoculated at the appropriate concentrations into 96-well plates using a multichannel pipette. After 24 hr, TGF-β1 (10 ng/ml and 20 ng/ml; Sigma) was added to the culture wells, and cultures were incubated for 24 hr and 48 hr at 37° C., under an atmosphere of 5% $CO_2$. MTT (3-(4,5-dimethylthiazol-2-yl)-2,5-diphenyltetrazolium bromide) (Sigma) solution at a concentration of 5 mg/ml was added to the media and the cells were further incubated for 4 hr. After replacing 100 µl of supernatant with 100 µl of DMSO, the absorbance of each well was determined at 540 nm with a SEAC (Sirio S) photometer (Italy). The percentage of cell survival was defined as the relative absorbance of treated versus untreated cells.

Example 6: Transduction and Flow Cytometry

A549 and hASC cells were transduced at an MOI of 50 and 200 respectively, with the different lentiviral constructs, in the presence of 8 µg/ml polybrene (Sigma). Forty-eight hours after transduction, cells were harvested, washed in phosphate-buffered saline (PBS) supplemented with 10% fetal calf serum and the percentage of eGFP positive cells was analyzed by flow cytometry (FACscalibur, BD)

Example 7: Protein Immunoblot (Western-Blot)

For Western blot analysis, both 20 µl and 100 µl of cell supernatant were loaded on 10% SDS-polyacrylamide gels, separated by electrophoresis and blotted onto Immovilon PVDF membranes (Millipore Corporation, Bedford, Mass., USA). The membrane was exposed to anti-TβRII monoclonal primary antibody (clone C-4) (Santa Cruz, Biotechnology) diluted 1/200, or the monoclonal antibody IM 0577 (unprotected)], capable of specifically detecting TβRII-SE, diluted 1/500. Horseradish peroxidase (HRP)-conjugated goat anti-mouse antibody (Becton Dickinson GmbH) diluted 1/10000 was used as secondary antibody. Protein detection was performed with the Amersham ECL Plus Western blotting detection reagents (Amersham Buchler GmbH, Germany) in a Typhoon 9410, Variable Mode Imager (GE Healthcare Bio-Sciences Aft Uppsala, Sweden).

Example 8: DNA and Protein Sequence Analysis cDNA sequences belonging to the different TβRII isoforms were used and the predicted protein sequences and statistics were obtained using the EditSeq software (DNAstar, Inc. Madison, Wis., USA). Both the DNA and the predicted protein sequences belonging to the TβRII-SE cDNA were aligned to known isoforms of the human TβRII receptor (A and B) using the MegAlign software (DNASTAR, Inc. Madison, Wis., USA).

Example 9: Analysis of Cytokines and Chemokines Secreted by hASC Cells

A cytokine/chemokine array kit G5 (Ray Biotech Inc., Norcross, Ga.) was used to detect a panel of 80 secreted cytokines as recommended by the manufacturer. hASCs P7 untransduced or transduced with lentiviral vectors were grown for 72 h in a medium supplemented with 0.1% BSA. Supernatants were collected, filtered and frozen after collection. For densitometry analysis of the arrays, Typhoon 9410 Variable mode Imager (GE Healthcare Life Sciences) was used, and signal intensity values were measured using the Image analysis software ImageQuant TL 7.0 (GE Healthcare Life Sciences). Microarray data were analyzed with RayBio® Antibody Array Analysis Tool. Good data quality and adequate normalization were ensured using internal control normalization without background. Any ≥1.5-fold increase or ≤0.65-fold decrease in signal intensity for a single analyte between samples or groups may be considered a measurable and significant difference in expression, provided that both sets of signals are well above background (Mean background+3 standard deviations, accuracy≈99%).

Example 10: Generation of Monoclonal and Polyclonal Antibodies Raised Against Human TβRII-SE Antibodies were generated by Rheabiotech, Campinas, Brazil. Immunization of both rabbit (polyclonal antibody) or mice (monoclonal antibody), was performed using a Multiple Antigen Peptide System (MAPS) with 8 identical copies of a peptide containing the 13 amino acids (FSKVHYEGKKKAW) (SEQ ID No. 12), which are only found in TβRII-SE and not in the other splicing variants of the receptor. The monoclonal antibody IM-0577 was developed in mice and purified by protein G affinity chromatography. Antibodies specificity was assayed by indirect ELISA by sensitization with antigen at a concentration of 5 µg/ml in Carbonate Buffer 0.2 M, blocked by PBS/BSA and detected with serial dilutions (1:1000-1:64000) of the specific antibody. The ELISA test was developed with a Horseradish peroxidase (HRP)-conjugated secondary antibody together with $H_2O_2$/OPD as chromogenic substrate, and detected by absorbance at 492 nM.

Example 11: In Vivo Study of Articular Cartilage Damage by Ciprofloxacin (CPFX) and the TβRII-SE Isoform Male 24-day-old Wistar rats were housed under controlled conditions at 21±1° C. with 50%±5% relative humidity and a constant light-dark schedule (light, 8 a.m. to 8 p.m.). Food and tap water was provided ad libitum. The rats received ciprofloxacin hydrochloride on day 24 by oral administration of 200 mg/kg of body weight during 10 days. The animals were examined for clinical abnormalities including motility alterations and weighted during the treatment period.

On day 14 after ciprofloxacin treatment, 50 µl viral vectors were injected intra-articularly with either Lt.coT-BRII-SE/Fc ($2.35 \times 10^6$ transducing Units, TU) or Lt.eGFP ($6 \times 10^6$ TU). Control animals without ciprofloxacin were treated in the same manner.

Example 12: Method to Treat Liver Fibrosis Using a Lentiviral Vector Encoding TβRII-SE/Fc Fusion Protein Male Wistar rats weighting 150-200 g were housed at Mar del Plata National University Laboratory Animal Unit at a mean constant temperature of 22° C. with a 12 h light-dark cycle, and free access to standard pellet chow and water. All experiments were performed according to the 'Guide for the Care and Use of Laboratory Animals' and approved by the Institutional Animal Care and Use Committee (CICUAL) of Mar del Plata National University. The experimental groups were designed as follows (n=7 per group): (I) Control group received intraperitoneal (ip) injection of vehicle of $CCl_4$; (II) $CCl_4$ group received ip injection of $CCl_4$; (III) Lv.TβRII-SE/Fc+$CCl_4$ group received intrahepatic (ih) injection of Lv.TβRII-SE/Fc (week 0) before treatment with $CCl_4$.

In Vivo Liver Transduction

Figure 34:
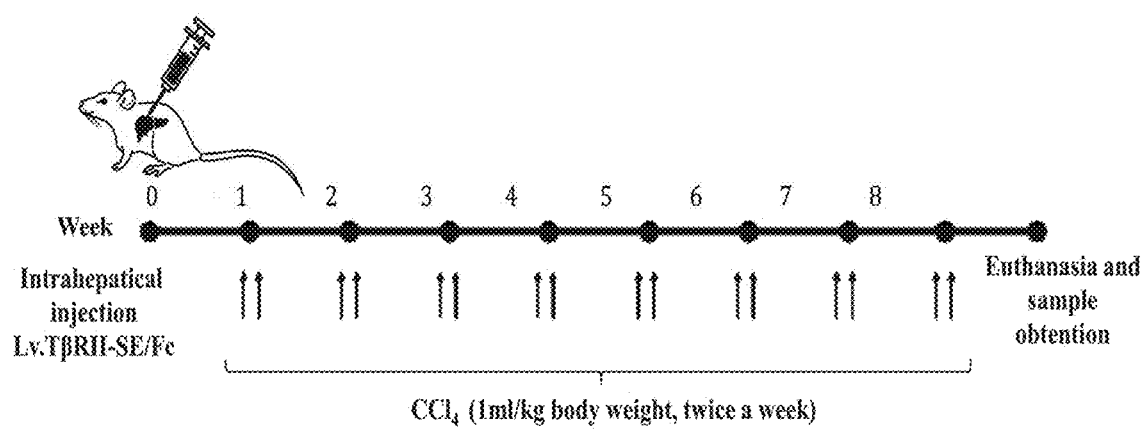
FIG. 34 shows the experimental design and time schedule of $CCl_4$ injection, administration of the lentiviral vector of the invention, and sample acquisition for analysis. Animals were euthanized by $CO_2$ inhalation after 72 hours of the last $CCl_4$ injection.

Animals were ih injected with Lv.TβRII-SE/Fc ($5-10 \times 10^7$ transduction units/ml) a week before the induction of liver fibrosis (FIG. 34). To employ this route of administration, a small incision was made in animals previously anesthetized with ketamine/xylazine (50 mg/5 mg/kg, ip injection). Livers were exposed and small volumes of the lentiviral vector were injected with a 30 G needle into several liver sites.

Liver Fibrosis Induction

Liver fibrosis was induced by ip injection of carbon tetrachloride ($CCl_4$) 1 ml in oil (1:1), per kg of body weight (BW), twice a week, for 8 weeks (FIG. 34), according to a well-established model (experimental groups II and III). Seventy-two hours after the last $CCl_4$ injection, animals were euthanized by $CO_2$ inhalation. Then, livers were obtained and fixed in 10% neutral buffered formalin for histological analysis. Serum was also collected from each animal to analyze biochemical parameters.

Body Weight Determinations

Body weight (BW) measurements were taken before each $CCl_4$ ip injection, and after completion of the experiment. These data were used to calculate BW gain, which was expressed as the percentage (%) of increase respect to the initial BW. After euthanasia, livers were harvested and weighted to calculate the liver to body weight ratio (LW/BW), also expressed as percentage.

Biochemical Parameter Determinations

Liver enzyme levels of aspartate aminotransferase (AST), alanine aminotransferase (ALT), and alkaline phosphatase (ALP) were determine in serum with an automatic analyzer BT300 plus (Biotecnica), according to the manufacturer's recommendations.

Histological Analysis

Livers fixed in 10% neutral buffered formalin were embedded in paraffin. Liver sections (5 µm) were stained with Hematoxylin and Eosin (H&E), for liver architecture visualization. For liver fibrosis assessment, sections were stained with 0.1% Sirius Red. Quantification of Sirius Red-positive areas was performed in at least ten microscopy fields per histological section using the software ImageJ. Results were expressed as mean percentage of Sirius Red-positive area per field.

Immuhistochemichal Analysis

For immunohistochemical analysis, 5 µm sections were dewaxed and rehydrated. Endogenous peroxidase activity was blocked with 3% $H_2O_2$ 3% in methanol (10 min, at room temperature). Antigen retrieval was performed using the heat induced epitope retrieval (HIER) method with 0.1 M citrate buffer, pH 6. Tissue sections were then incubated for 12-16 h at 4° C. with rabbit anti-α-smooth muscle actin (anti-α-SMA, 1:500, Cell Signaling Technology, Danvers, Mass.). After two washes with PBS, slides were incubated with HiDef Detection amplifier Mouse and Rabbit (Cell Marque, Rocklin, Calif.) for 10 min, at room temperature. Sections were further washed with PBS and incubated with HiDef Detection HRP Polymer Detector (Cell Marque, Rocklin, Calif.) for 10 min, at room temperature. Finally, sections were washed twice with PBS, and immunohistochemical staining was obtained using the DAB Chromogen kit (Cell Marque, Rocklin, Calif.) by 5 min. incubation at room temperature, and counterstained with Hematoxylin. Dehydrated sections were mounted and imaged on a Nikon Eclipse E200 microscope.

Statistical Analysis

Data were analyzed using two-way ANOVA followed by the Fisher's Least Significant Difference (LSD) test. Statistical significance was set at <0.05. Results are expressed as mean±SD.

Example 13: Method to Treat Cancer with a Lentiviral Vector Encoding TβRII-SE/Fc Fusion Protein TN60 murine mammary carcinoma cells were injected subcutaneously into syngenic C3H/S mice (N=6-7 per group), as it is described by García M. et al., 2015 *Biological Rhythm Research* 46: 573-578. Ten days after, $1.5 \times 10^6$ transduction units of a lentiviral vectors encoding TβRII-SE/Fc (Lv.TβRII-SE/Fc) (N=7), or the control vector Lv.TβRII-DN (dominant negative) (N=6) were intratumorally injected. As an additional control, mice were intratumorally injected with the same volume of culture medium (vehicle).

Tumor diameter was determine every 2-3 days by measuring the tumor perimeter with a digital caliper, Tumor mean volume was determine by the formula $V=4/3 (p \times r^3)$. Two weeks after tumor implantation, mice were euthanized by cervical dislocation.

Example 14: Method to Determine Rheumatoid Arthritis Disease Activity by TβRII-SE Protein Quantification in Neutrophils by Immune Detection with the Anti TβRII-SE Monoclonal Antibody Patients Volunteers and Samples Peripheral blood was collected by venipuncture from 19 RA patients diagnosed according to the ACR/EULAR 2010 criteria. All procedures were approved by CER Medical Institute Research Ethics Committee, and the Comisión Conjunta de Investigación en Salud, Department of Health, Buenos Aires Province, Argentina, registered under the number 2919/653/13. All procedures were performed after signing off a voluntary informed consent, by the donors. Exclusion criteria included severe anaemia, autoimmune diseases different from RA, any other disease/condition able to increase ESR, treatment with biological drugs, treatment with disease-modifying anti-rheumatic drugs (DMARDs) except methotrexate, and with drugs with known effect on the TGF-β signalling cascade (losartan).

Detection of TβRII-SE in neutrophils by Flow Cytometry: both neutrophils and peripheral blool mononuclear cells (PBMC) were isolated by Ficoll-Paque™ PLUS density gradient. Red blood cells were eliminated from the neutrophil fraction by incubation with a hypertonic buffer (0.15 M $NH_4Cl$, 10 mM $KHCO_3$, 0.1 mM EDTA). To determine the percentage of cells expressing TβRII-SE, $1 \times 10^6$ of both, neutrophils and PBMC were fixed and permeabilized with the Cytofix/Cytoperm Kit (BD Biosciences, USA) Subsequently, cells were incubated with 0.5 μg of the anti-TβRII-SE monoclonal antibody of the invention conjugated with the fluorochrome ATTO 647N. Cells were resuspended in 100 μl of PBS and were analyzed by Flow Cytometry in a FACSCalibur device (BD Biosciences, USA), using Flowjo software (BD Biosciences, USA). The percentage of neutrophils expressing TβRII-SE was determined by taking as cut off the fluorescence value obtained with lymphocytes of each patient, as reference. TβRII-SE fluorescence values in neutrophils were correlated with DAS28-ESR disease activity scores by the Spearman's rank correlation test of the OriginPro 8.5.1 software (Origin Lab Corporation, Northampton, Mass., USA).

Example 15: Detection of TβRII-SE in Neutrophils by in-Cell ELISA

To develop a method to quantify intracellular TβRII-SE in leukocytes by In-cell ELISA in RA pacientes, $2.6 \times 10^6$ células/cm$^2$, in saline solution$^{+2}$ (0.9% NaCl, 1 mM $MgCl_2$, 1 mM $CaCl_2$)), were incubated in 96 well plates for 20 minutes at room temperature, to allow cell adherence to plastic. Subsequently, cells were washed twice with 1×PBS, and fixed and permeabilized with 100 μL of Fix/Perm solution (BD Cytofix/Cytoperm™, USA) for 20 min. at 4° C. After two washes with 250 μL of 1×BD Perm/Wash buffer (BD Perm/Wash™ USA), adhered cells were incubated with the anti-TβRII-SE antibody (10 μg/mL in 50 μL of BD Perm/Wash buffer) for 30 minutes to 16 hours at 4° C. As control, cells were also incubated without the above mentioned antibody. After two additional washes with 250 μL of 1×BD Perm/Wash Buffer, cells were incubated with 1 μg/mL secondary antibody (Anti Mouse HRP conjugated—Promega, USA), in 50 μL de 1×BD Perm/Wash Buffer, for 90 minutes. Subsequently, cells were incubated with 100 μL of quenching solution (10% V/V $H_2O_2$ in 1×BD Perm/Wash Buffer. After 3 washes with 250 μL of 1×BD Perm/Wash Buffer, cells were incubated with 100 μL of TMB substrate (Life Technologies, EEUU), in the dark, and 655 nm absorbance was determined every 5 minutes for 30 minutes, in a microplate reader (Biotek, SYNERGY™ H1, USA). In addition, the number of adhered cells was determined by cristal violet staining, to be used as In-cell ELISA normalizer. To this end, each well was washed four times with 200 μL 1×PBS and cells were incubated with 50 μl crystal violet solution containing 2 g de crystal violet (Sigma, USA), 20 ml 95% ethanol, 0.8 g amonium oxalate, and 80 ml distilled water, for 30 minutes at room temperature. After washing the wells with abundant tap water, cells were incubated with 100 μL of 1% SDS for 60 minutes at room temperature. Finally, absorbance at 595 nm was determined in a microplate reader (Biotek, SYNERGY™ H1, USA).

Intracellular TβRII-SE relative concentration values were determined as follows:

$$AbsNn = Absn_{655}/Absn_{595}$$

$$AbsNT = AbsT_{655}/AbsT_{595}$$

$$TβRII\text{-}SE \text{ relative concentration} = (AbsNT - AbsNn) * 100$$

where:

AbsNT=normalized absorbance of the well containing Anti TβRII-SE primary antibody.

$AbsT_{655}$=Absorbance at 655 nm of the well containing Anti TβRII-SE primary antibody.

$AbsT_{595}$=Absorbance at 595 nm of the well containing Anti TβRII-SE primary antibody.

AbsNn=normalized absorbance of the well without primary antibody (negative).

$Absn_{655}$=Absorbance at 655 nm of the well without primary antibody (negative).

$Absn_{595}$: Absorbance at 595 nm of the well without primary antibody (negative).

TβRII-SE relative concentration in plastic adhered leukocytes from RA patients was correlated with their matching DAS28-ESR value using the Spearman rank correlation test of the OriginPro 8.5.1 software (Origin Lab Corporation, Northampton, Mass., USA).

---

What is claimed is:

1. A fusion peptide comprising the endogenous soluble isoform of the TGF beta receptor II (TβRII-SE) fused to a ligand, wherein the isoform consists of the amino acid sequence set forth in SEQ ID No. 2.

2. The peptide according to claim 1, wherein the ligand is an immunoglobulin Fc portion.

3. The peptide according to claim 1, wherein said peptide is codified by the polynucleotide sequence set forth in SEQ ID No. 7.

4. A vector comprising at least the polynucleotide of claim 3.

5. The vector according to claim 4, wherein the vector is a lentivirus.

* * * * *

UNITED STATES PATENT AND TRADEMARK OFFICE
CERTIFICATE OF CORRECTION

PATENT NO. : 11,072,647 B2  
APPLICATION NO. : 16/173426  
DATED : July 27, 2021  
INVENTOR(S) : Ana Romo et al.

Page 1 of 1

It is certified that error appears in the above-identified patent and that said Letters Patent is hereby corrected as shown below:

On the Title Page

Item (54) and in the Specification, Column 1, Lines 1-3 should read:
TGF- β RECEPTOR II ISOFORM, FUSION PEPTIDE, METHODS OF TREATMENT AND METHODS IN VITRO

(73) Assignees should read:
Consejo Nacional de Investigacion Científica y Tecnicas, Buenos Aires (AR); Fundacion Articular, Buenos Aires (AR); INIS Biotech LLC, Delaware, (US)

Signed and Sealed this  
First Day of February, 2022

Drew Hirshfeld  
*Performing the Functions and Duties of the*  
*Under Secretary of Commerce for Intellectual Property and*  
*Director of the United States Patent and Trademark Office*

UNITED STATES PATENT AND TRADEMARK OFFICE
CERTIFICATE OF CORRECTION

PATENT NO. : 11,072,647 B2
APPLICATION NO. : 16/173426
DATED : July 27, 2021
INVENTOR(S) : Ana Romo et al.

It is certified that error appears in the above-identified patent and that said Letters Patent is hereby corrected as shown below:

On the Title Page

Column 1, (73) Assignees should read:
Consejo Nacional de Investigaciones Cientificas y Tecnicas, Buenos Aires (AR); Fundacion Articular, Buenos Aires (AR); INIS Biotech LLC, Delaware, US This certificate supersedes the Certificate of Correction issued February 1, 2022.

Signed and Sealed this
Twentieth Day of September, 2022

Katherine Kelly Vidal
*Director of the United States Patent and Trademark Office*

SEQUENCE LISTING

<160> NUMBER OF SEQ ID NOS: 12

<210> SEQ ID NO 1
<211> LENGTH: 249
<212> TYPE: DNA
<213> ORGANISM: Homo sapiens

<400> SEQUENCE: 1

-continued

```
accggtatgg gtcgggggct gctcaggggc ctgtggccgc tgcacatcgt cctgtggacg    60
cgtatcgcca gcacgatccc accgcacgtt cagaagtcgg ttaataacga catgatagtc   120
actgacaaca acggtgcagt caagtttcca caactgtgta aattttgtga tgtgagattt   180
tccacctgtg acaaccagaa atcctgcttc tccaaagtgc attatgaagg aaaaaaaaaa   240
gcctggtga                                                           249
```

<210> SEQ ID NO 2
<211> LENGTH: 80
<212> TYPE: PRT
<213> ORGANISM: Homo sapiens

<400> SEQUENCE: 2

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Phe Ser Lys Val His Tyr Glu Gly Lys Lys Lys Ala Trp
65                  70                  75                  80
```

<210> SEQ ID NO 3
<211> LENGTH: 189
<212> TYPE: PRT
<213> ORGANISM: Homo sapiens

<400> SEQUENCE: 3

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
            85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr
            180                 185
```

<210> SEQ ID NO 4

```
<211> LENGTH: 82
<212> TYPE: PRT
<213> ORGANISM: Homo sapiens

<400> SEQUENCE: 4

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Phe Ser Lys Val His Tyr Glu Gly Lys Lys Lys Ala Trp
65                  70                  75                  80

Arg Ser

<210> SEQ ID NO 5
<211> LENGTH: 258
<212> TYPE: DNA
<213> ORGANISM: Homo sapiens

<400> SEQUENCE: 5
accggtgcca ccatgggaag aggtctcctc agaggactct ggccactgca catcgtcctg      60
tggaccagaa tcgcatctac catccctcct catgtgcaga atctgtcaa caatgacatg     120 atcgtcacag acaacaacgg tgctgtgaag tttcctcagc tgtgtaagtt ctgcgacgtc     180
aggttcagta cctgcgacaa tcagaaatct tgtttcagca aggtgcacta cgaagggaag     240
aagaaagcat ggagatct                                                  258

<210> SEQ ID NO 6
<211> LENGTH: 305
<212> TYPE: PRT
<213> ORGANISM: Homo sapiens

<400> SEQUENCE: 6

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Phe Ser Lys Val His Tyr Glu Gly Lys Lys Lys Ala Trp
65                  70                  75                  80

Arg Ser Asp Lys Thr His Thr Cys Pro Pro Cys Pro Ala Pro Glu Leu
                85                  90                  95

Leu Gly Gly Pro Ser Val Phe Leu Phe Pro Pro Lys Pro Lys Asp Gln
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160
```

```
Thr Tyr Arg Val Val Ser Val Leu Thr Val Leu His Gln Asp Trp Leu
            165                 170                 175
Asn Gly Lys Glu Tyr Lys Cys Lys Val Ser Asn Lys Ala Leu Pro Ala
        180                 185                 190
Pro Ile Glu Lys Thr Ile Ser Lys Ala Lys Gly Gln Pro Arg Glu Pro
    195                 200                 205
Gln Val Tyr Thr Leu Pro Pro Ser Arg Glu Glu Met Thr Lys Asn Gln
210                 215                 220
Val Ser Leu Thr Cys Leu Val Lys Gly Phe Tyr Pro Ser Asp Ile Ala
225                 230                 235                 240
Val Glu Trp Glu Ser Asn Gly Gln Pro Glu Asn Asn Tyr Lys Thr Thr
            245                 250                 255
Pro Pro Val Leu Asp Ser Asp Gly Ser Phe Phe Leu Tyr Ser Lys Leu
        260                 265                 270
Thr Val Asp Lys Ser Arg Trp Gln Gln Gly Asn Val Phe Ser Cys Ser
    275                 280                 285
Val Leu His Glu Ala Leu His Asn His Tyr Thr Gln Lys Ser Leu Ser
290                 295                 300
Leu
305

<210> SEQ ID NO 7
<211> LENGTH: 930
<212> TYPE: DNA
<213> ORGANISM: Homo sapiens

<400> SEQUENCE: 7
accggtgcca ccatgggaag aggtctcctc agaggactct ggccactgca catcgtcctg      60
tggaccagaa tcgcatctac catccctcct catgtgcaga atctgtcaa caatgacatg     120
atcgtcacag acaacaacgg tgctgtgaag tttcctcagc tgtgtaagtt ctgcgacgtc    180
aggttcagta cctgcgacaa tcagaaatct tgtttcagca aggtgcacta cgaagggaag    240
aagaaagcat ggagatctga caaaactcac acatgcccac cgtgcccagc acctgaactc    300
ctggggggac cgtcagtctt cctcttcccc ccaaaaccca aggaccaact gatgatctcc    360
cggacccctg aggtcacatg cgtggtggtg gacgtgagcc acgaagaccc tgaggtcaag    420
ttcaactggt acgtggacgg cgtggaggtg cataatgcca agacaaagcc gcggaggag     480
cagtacaaca gcacgtaccg tgtggtcagc gtcctcaccg tcctgcacca ggactggctg    540
aatggcaagg agtacaagtg caaggtctcc aacaaagccc tcccagcccc catcgagaaa    600
accatctcca aagccaaagg gcagccccga gaaccacagg tgtacaccct gcccccatcc    660
cgggaggaga tgaccaagaa ccaggtcagc ctgacctgcc tggtcaaagg cttctatccc    720
agcgacatcg ccgtggagtg ggagagcaat gggcagccgg agaacaacta caagaccacg    780
cctcccgtgc tggactccga cggctccttc ttcctctaca gcaagctcac cgtggacaag    840
agcaggtgg agcaggggaa cgtcttctca tgctccgtgc tgcatgaggc tctgcacaac    900
cactacacgc agaagagcct ctccctgtaa                                    930

<210> SEQ ID NO 8
<211> LENGTH: 24
<212> TYPE: DNA
<213> ORGANISM: Artificial Sequence
<220> FEATURE:
<223> OTHER INFORMATION: primer 1

<400> SEQUENCE: 8
```

```
agatctgaca aaactcacac atgc                                          24

<210> SEQ ID NO 9
<211> LENGTH: 22
<212> TYPE: DNA
<213> ORGANISM: Artificial Sequence
<220> FEATURE:
<223> OTHER INFORMATION: primer 2

<400> SEQUENCE: 9
gatatcttta cccggagaca gg                                            22

<210> SEQ ID NO 10
<211> LENGTH: 24
<212> TYPE: DNA
<213> ORGANISM: Artificial Sequence
<220> FEATURE:
<223> OTHER INFORMATION: primer 3

<400> SEQUENCE: 10
accggtatgg gtcgggggct gctc                                          24

<210> SEQ ID NO 11
<211> LENGTH: 25
<212> TYPE: DNA
<213> ORGANISM: Artificial Sequence
<220> FEATURE:
<223> OTHER INFORMATION: primer 4

<400> SEQUENCE: 11
gtcgactcag tagcagtaga agatg                                         25

<210> SEQ ID NO 12
<211> LENGTH: 13
<212> TYPE: PRT
<213> ORGANISM: Homo sapiens

<400> SEQUENCE: 12

Phe Ser Lys Val His Tyr Glu Gly Lys Lys Lys Ala Trp
1               5                   10
```